United States Patent
Imam et al.

(10) Patent No.: US 12,077,747 B2
(45) Date of Patent: *Sep. 3, 2024

(54) RECOMBINANT ALGAE HAVING HIGH LIPID PRODUCTIVITY

(71) Applicant: Viridos, Inc., La Jolla, CA (US)

(72) Inventors: Saheed Imam, La Jolla, CA (US); Eric R. Moellering, San Diego, CA (US); Luke Peach, La Jolla, CA (US); William F. Lambert, San Diego, CA (US); Jessica Weir, San Diego, CA (US)

(73) Assignee: Viridos, Inc., La Jolla, CA (US)

( * ) Notice: Subject to any disclaimer, the term of this patent is extended or adjusted under 35 U.S.C. 154(b) by 162 days.

This patent is subject to a terminal disclaimer.

(21) Appl. No.: 17/470,925

(22) Filed: Sep. 9, 2021

(65) Prior Publication Data

US 2022/0090002 A1   Mar. 24, 2022

Related U.S. Application Data

(60) Provisional application No. 63/077,474, filed on Sep. 11, 2020.

(51) Int. Cl.
| | |
|---|---|
| *C12N 1/12* | (2006.01) |
| *C12N 15/82* | (2006.01) |
| *C12P 7/649* | (2022.01) |
| *C12R 1/89* | (2006.01) |

(52) U.S. Cl.
CPC ........... *C12N 1/12* (2013.01); *C12N 15/8213* (2013.01); *C12P 7/649* (2013.01); *C12R 2001/89* (2021.05)

(58) Field of Classification Search
CPC ...... C12N 9/22; C12N 15/102; C12N 15/113; C12N 15/11; C12N 9/1276; C12N 15/82; C12Y 207/07049; Y02E 50/10

USPC .......................................................... 435/463
See application file for complete search history.

(56) References Cited

U.S. PATENT DOCUMENTS

| | | |
|---|---|---|
| 2018/0186842 A1 | 7/2018 | Moellering et al. |
| 2019/0203221 A1 | 7/2019 | Ajjawi et al. |

OTHER PUBLICATIONS

Devos et al., (Proteins: Structure, Function and Genetics, 2000, vol. 41: 98-107.*
Whisstock et al., (Quarterly Reviews of Biophysics 2003, vol. 36 (3): 307-340.*
Witkowski et al., (Biochemistry 38:11643-11650, 1999.*
Kisselev L., (Structure, 2002, vol. 10: 8-9.*
PCT International Search Report and Written Opinion in International Application No. PCT/US2021/049708, dated Feb. 4, 2022, 12 pages.

* cited by examiner

*Primary Examiner* — Robert B Mondesi
*Assistant Examiner* — Mohammad Y Meah
(74) *Attorney, Agent, or Firm* — DLA Piper LLP (US)

(57) ABSTRACT

The invention provides recombinant algal organisms that have a genetic modification to a gene or nucleic acid sequence encoding an RNA binding domain. In some embodiments the genetic modification can be a functional deletion or attenuation of the gene. The genetic modification results in a mutant organism with increased lipid productivity and/or higher biomass productivity. The lipid products of these mutants can be utilized as biofuels or to manufacture other specialty products. The recombinant mutants can also, optionally, have a genetic modification to a gene encoding an SGI1 polypeptide. Methods of making and using the recombinant algal mutants and methods of producing lipids are also disclosed.

Figure 1A:
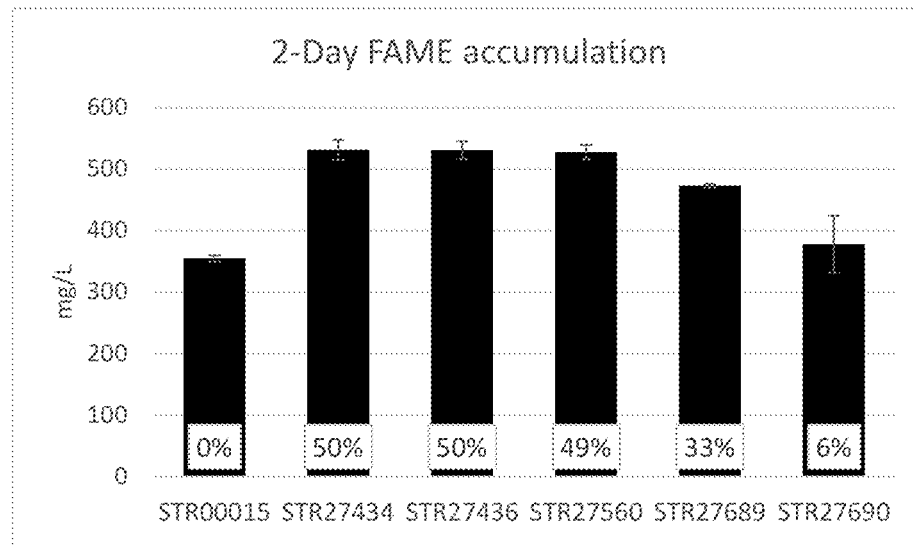

25 Claims, 8 Drawing Sheets
Specification includes a Sequence Listing.

RECOMBINANT ALGAE HAVING HIGH LIPID PRODUCTIVITY

CROSS-REFERENCE TO RELATED APPLICATIONS

This application claims benefit of priority under 35 U.S.C. § 119(e) of U.S. Ser. No. 63/077,474, filed Sep. 11, 2020, the entire contents of which is incorporated herein by reference in its entirety.

INCORPORATION OF SEQUENCE LISTING

The material in the accompanying sequence listing is hereby incorporated by reference into this application. The accompanying sequence listing text file name, SGI2280-1_Sequence_Listing.txt, was created Sep. 9, 2021, and is 72.5 kb. The file can be accessed using Microsoft Word on a computer that uses Windows OS.

FIELD OF THE INVENTION

The invention involves the provision of a recombinant mutant algal organism and methods for the production of lipids.

BACKGROUND OF THE INVENTION

The production of biofuels presents great opportunities to develop environmentally sound sources of energy that can be obtained at reasonable cost. Efforts have been directed towards using algae or other microorganisms to produce hydrocarbons that can be used as biodiesel or other biofuels due to their high lipid content. Additional specialty chemicals can also be obtained from these organisms and for use in consumer products.

Since algae use energy from sunlight to combine water and carbon dioxide to produce biomass, achieving increased productivity offers the possibility of a carbon neutral fuel source. The development of algal strains with very high lipid productivity for the production of algal-sourced biofuels therefore presents the possibility of a significant reduction in new carbon dioxide released into the atmosphere and a consequent reduction in the problem of global warming.

The development of commercially viable algal biofuels requires strains with high lipid and biomass productivity. Even the most productive wild type strains are not sufficiently productive to permit an economically viable development of this resource. Strategies for increasing algal production of biofuels and other products have included modification of nutrition provided to the organisms, such as cultivating the organisms in nitrogen, phosphorus, or silicon deficient media. Other strategies have included modification of cultivation conditions or environmental protocols, or various efforts directed towards genetic engineering of the organisms. While engineering algae strains to have a combination of increased photosynthetic efficiency (resulting in increased overall biomass productivity) and/or high lipid productivity could provide a solution to this problem, deficiencies still remain. The development of higher performing strains continues to be a barrier to efficient utilization of this energy source.

SUMMARY OF THE INVENTION

The invention provides recombinant algal organisms that have a genetic modification to a gene encoding an RNA binding domain. The genetic modification can be a functional deletion or attenuation of the gene. The genetic modification results in a mutant organism with increased lipid productivity and/or higher biomass productivity. The lipid products of these mutants can be utilized as biofuels or to manufacture other specialty products. The recombinant mutants can also, optionally, have a genetic modification to a gene encoding an SGI1 polypeptide. Methods of making and using the recombinant algal mutants and methods of producing lipids are also disclosed.

In a first aspect the invention provides a recombinant algal organism having a genetic modification in a gene encoding an RNA binding domain. The recombinant algal organism exhibits higher lipid productivity versus a corresponding control algal organism not having the genetic modification. In one embodiment the organism is a Chlorophyte alga. The organism can be a Chlorophyte alga of the Class Trebouxiophyceae. In one embodiment the gene encoding the RNA binding domain has a sequence having at least 80% sequence identity to SEQ ID NO: 1 or SEQ ID NO: 2. In one embodiment the genetic modification can be a functional deletion. The genetic modification can result in an attenuation in expression of the encoded RNA binding domain; and in one embodiment the genetic modification occurs in a regulatory sequence of the gene encoding the RNA binding domain. In one embodiment the regulatory sequence is a promoter. The genetic modification can be a deletion, disruption, or inactivation of the promoter. In one embodiment the genetic modification involves the deletion of one or more amino acids of the encoded RNA binding domain. The genetic modification can result in the deletion of at least one amino acid in the encoded RNA binding domain sequence.

In one embodiment the genetic modification is an insertion of a stop codon in a sequence encoding the RNA binding domain. In different embodiments the genetic modification can be a deletion, a disruption, or an inactivation. In one embodiment the genetic modification can be a knock out mutation. The recombinant alga can have at least 30% higher lipid productivity versus a control algae; or at least 50% higher lipid productivity versus a control algae. In one embodiment the recombinant alga produces at least 60 grams per square meter of lipid product after 5 days of cultivation. The recombinant alga can, optionally, have higher biomass productivity per unit time versus the corresponding control algal cell or organism, which in one embodiment can be measured as total organic carbon (TOC).

In one embodiment the recombinant alga has higher biomass productivity under nitrogen deficient conditions. The recombinant alga can have higher total organic carbon production under nitrogen deficient conditions.

In various embodiments the recombinant alga can be from family selected from the group consisting of: Oocystaceae, Chlorellaceae, and Eustigmatophyceae. In various embodiments the recombinant alga can be of a genus selected from *Chlorella, Parachlorella, Picochlorum, Tetraselmis*, or *Oocystis*. In some embodiments the recombinant alga can also have a genetic modification to a gene encoding an SGI1 polypeptide. In one embodiment the SGI1 polypeptide can have at least 80% sequence identity to SEQ ID NO: 14. In one embodiment the recombinant alga is an alga of the genus *Oocystis*.

In another aspect the invention provides a lipid produced by a recombinant alga of the invention.

In another aspect the invention provides a biomass product containing the recombinant alga of the invention.

In another aspect the invention provides a method of producing a composition containing lipids. The method involves performing a genetic modification to an algal organism in a gene encoding an RNA binding domain; cultivating the organism, and thereby producing a composition containing lipids. The method can be utilized with any recombinant alga of the invention.

In another aspect the invention provides methods of identifying a recombinant algal organism with high lipid productivity. The methods involve mutagenizing a population of algal organisms; screening the mutagenized algal organisms for higher lipid productivity; sequencing at least a portion of the genome of the mutagenized algal organisms; identifying genetic changes in the mutagenized organisms compared to the population of algal organisms prior to mutagenesis; recapitulating the genetic changes in a parental strain of the mutagenized algal organisms; to thereby identifying a recombinant algal organism having high lipid productivity. The methods can also involve a step of harvesting a lipidic composition from the algal organism. The recombinant algal organism identified can be any recombinant algal organism of the invention described herein. In one embodiment the genetic change can be a deletion, disruption, or inactivation of a sequence encoding an RNA binding domain or of a regulatory sequence thereof. The RNA binding domain can have at least 90% sequence identity to any one of SEQ ID NO: 1-3.

In another aspect the invention provides a method of producing a lipid containing composition. The method involves cultivating a recombinant algal cell or organism described herein to thereby produce a lipid containing composition. In one embodiment the method includes a step of harvesting the lipid from the lipid containing composition. The method can also include a step of purifying the lipid containing composition to produce a biofuel. The algal cell or organism can be any described herein. The gene encoding the RNA binding domain can have a sequence having at least 80% sequence identity to SEQ ID NO: 1 or SEQ ID NO: 2, or any sequence described herein. In one embodiment the genetic modification is a deletion, a disruption, or an inactivation. In various embodiments the recombinant alga is of a genus selected from *Chlorella*, *Parachlorella*, *Picochlorum*, *Tetraselmis*, and *Oocystis*.

DETAILED DESCRIPTION OF THE DRAWINGS

Figure 1B:
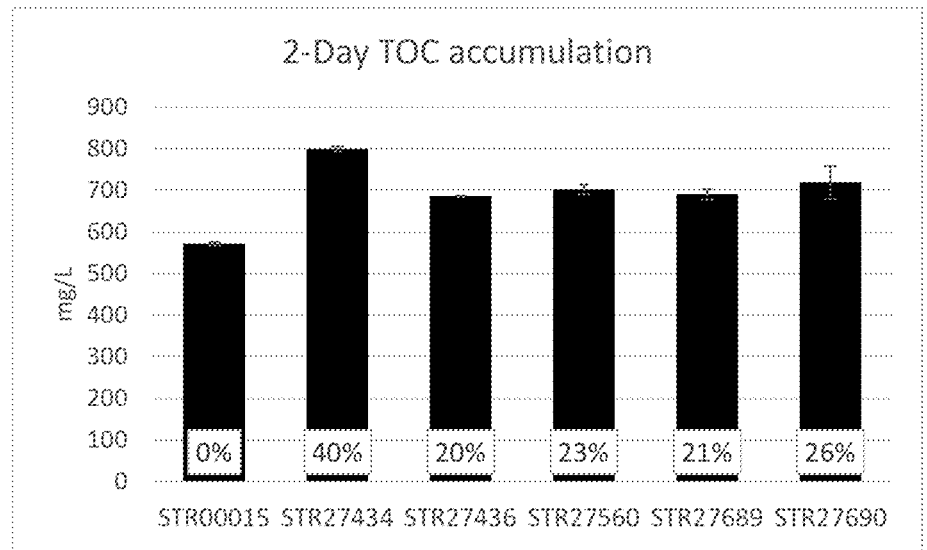
Figure 1C:
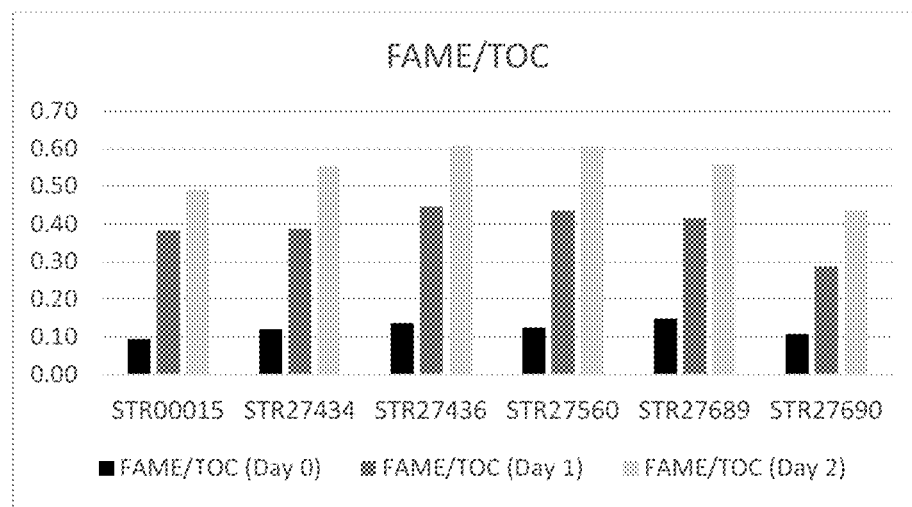

FIGS. 1a-1c; FIG. 1a is a graphical illustration of 2 day FAME accumulation in mutagenized lines versus the parental wild-type Strain 15. FIG. 1b is a graphical illustration of 2 day total organic carbon (TOC) accumulation in mutagenized lines versus the parental wild-type Strain 15. FIG. 1c is a graphical illustration of the FAME/TOC ratio in mutagenized lines versus the parental wild-type Strain 15, as an indicator of carbon partitioning.

Figure 2A:
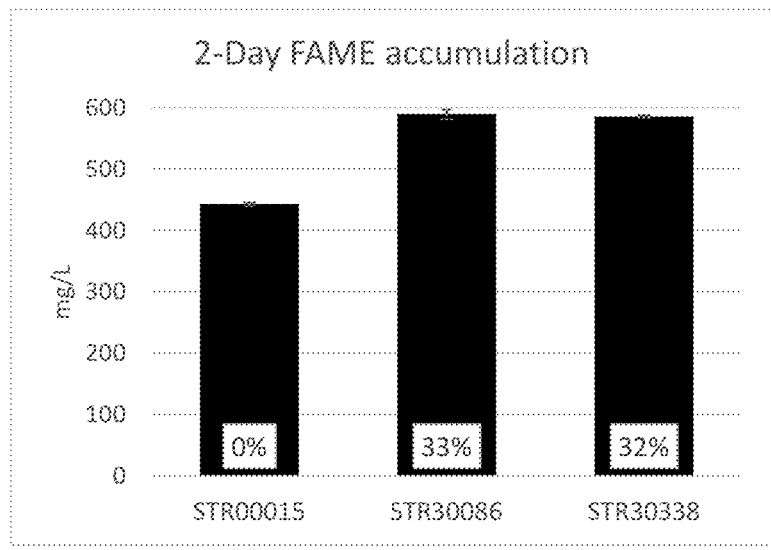
Figure 2B:
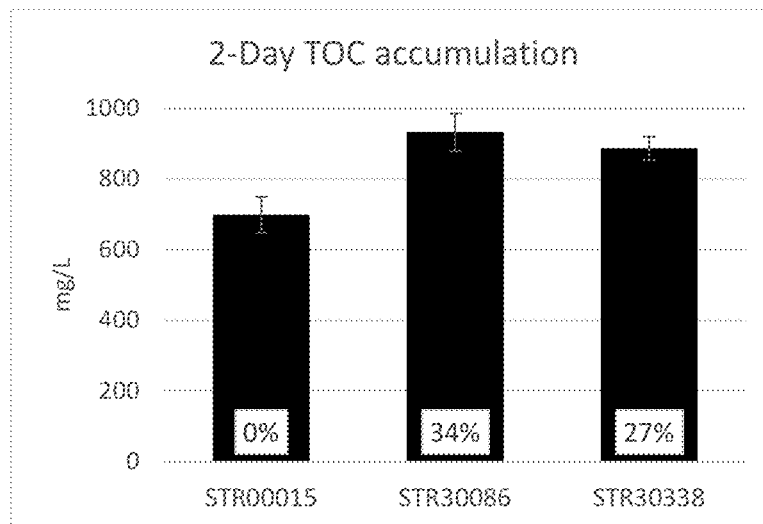
Figure 2C:
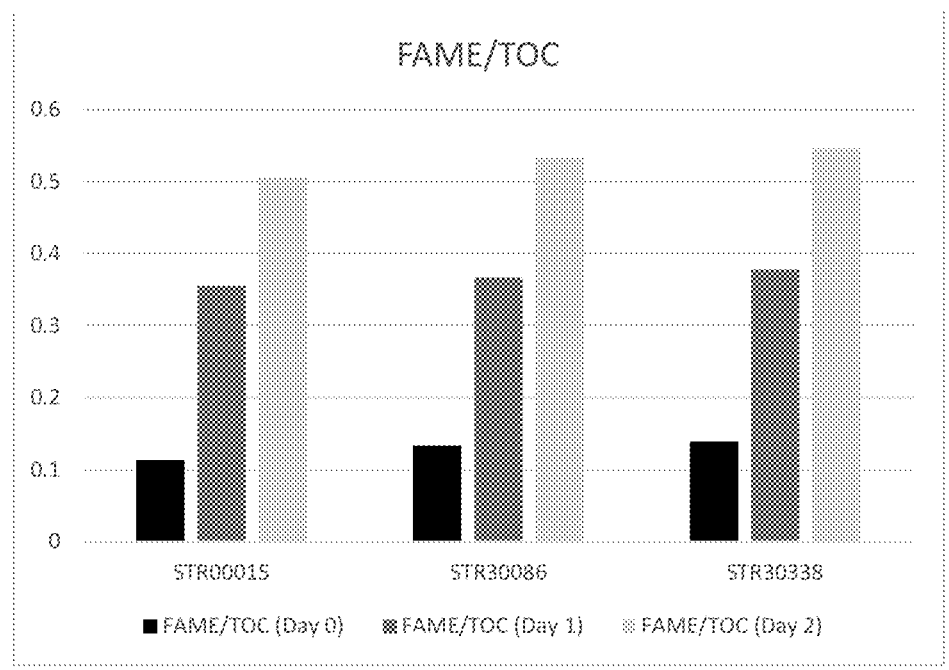

FIGS. 2a-2c; FIG. 2a is a graphical illustration of 2-day FAME accumulation in a wild-type (Strain 15) strain versus engineered strains having a knock out in gene '8676 (RNA binding domain) lines (Strain '086 and '338). FIG. 2b is a graphical illustration of 2-day total organic carbon (TOC) accumulation in a wild-type (Strain 15) strain versus engineered strains having a knock out in gene '8676 (RNA binding domain) lines (Strain '086 and '338). FIG. 2c is a graphical illustration of the FAME/TOC ratio of a wild-type (Strain 15) strain versus engineered strains having a knock out in gene '8676 (RNA binding domain) lines (Strain '086 and '338).

Figure 3A:
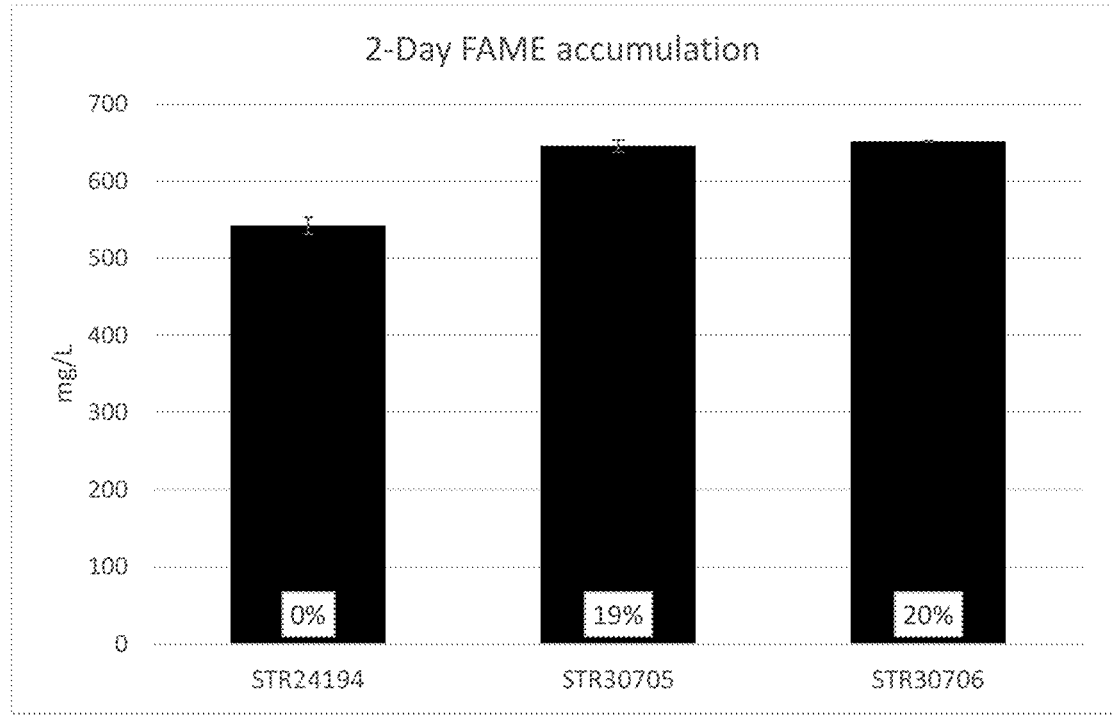
Figure 3B:
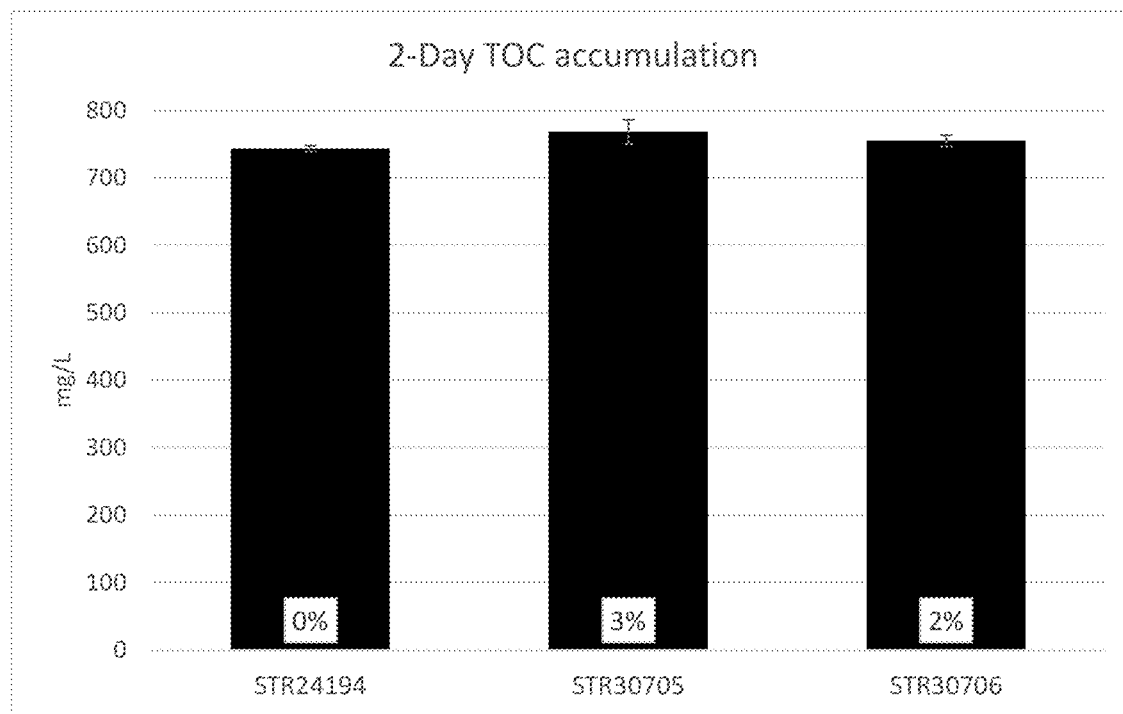
Figure 3C:
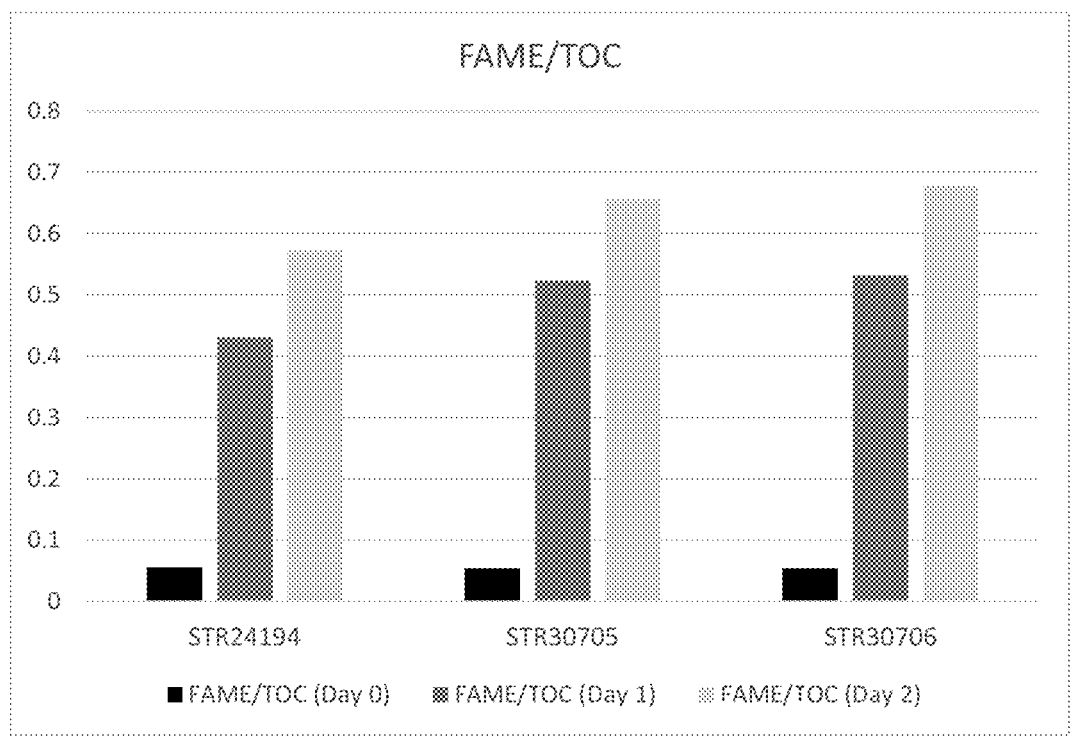

FIGS. 3a-3c; FIG. 3a is a graphical illustration of FAME accumulation in a laboratory background strain (Strain '194) strain versus engineered strains having a knock out in gene '8676 (RNA binding domain) lines (Strain '705 and '706). FIG. 3b is a graphical illustration of total organic carbon (TOC) accumulation in a laboratory background strain (Strain '194) strain versus engineered strains having a knock out in gene '8676 (RNA binding domain) lines (Strain '705 and '706). FIG. 3c is a graphical illustration of the FAME/TOC ratio of a laboratory background strain (Strain '194) strain versus engineered strains having a knock out in gene '8676 (RNA binding domain) lines (Strain '705 and '706).

Figure 4A:
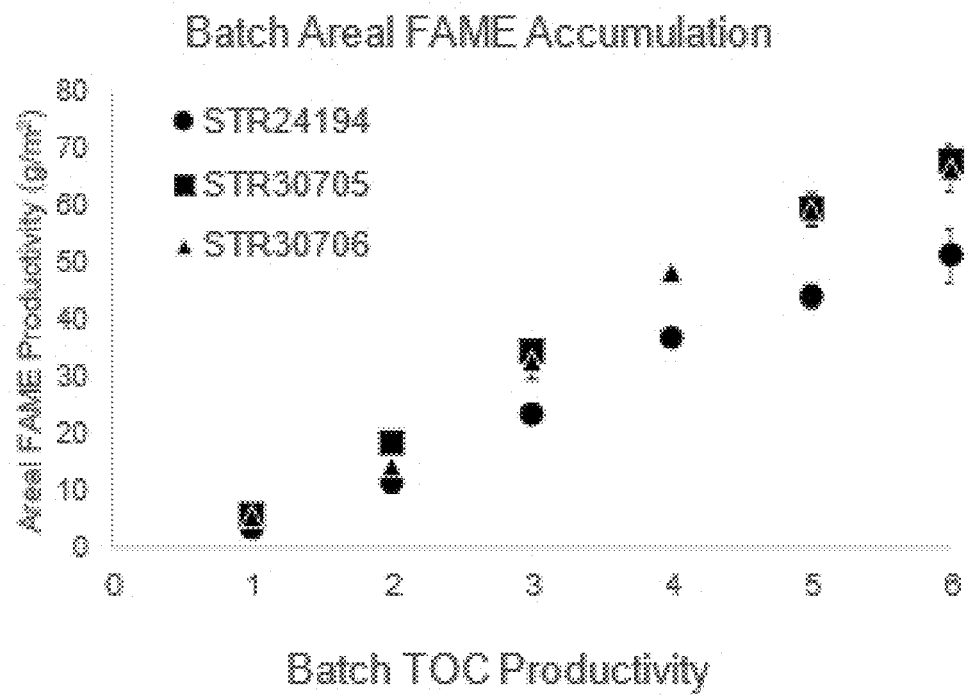
Figure 4B:
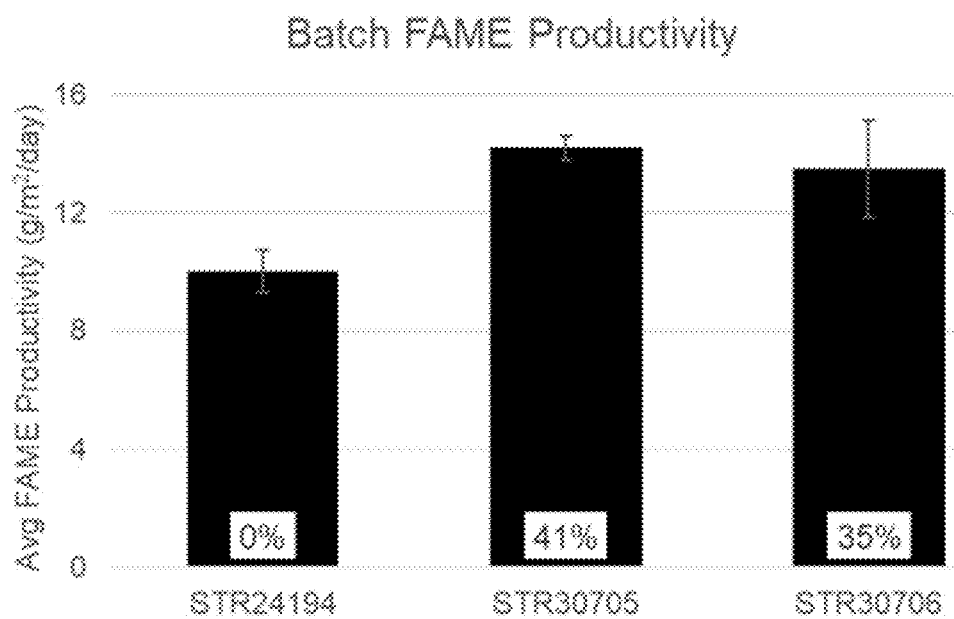
Figure 4C:
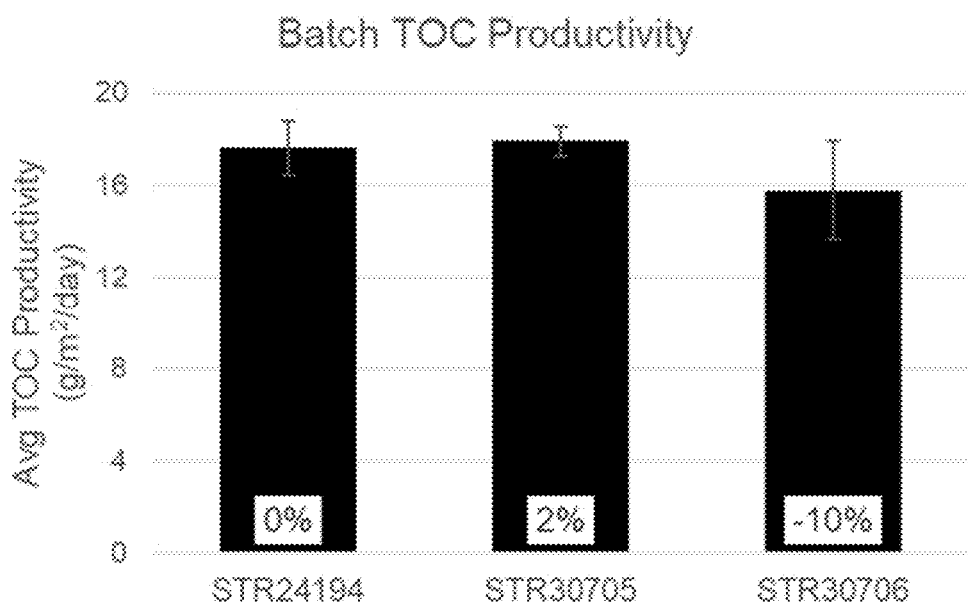
Figure 4D:
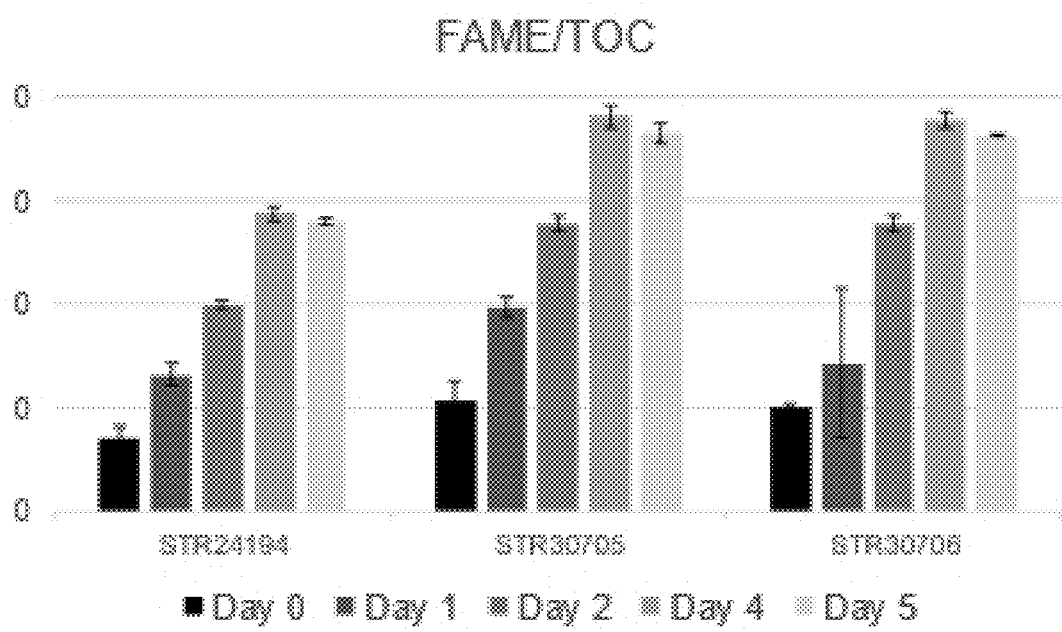

FIGS. 4a-4d; FIG. 4a provides a graphical illustration showing a linear increase in areal FAME productivity versus time (days) for the genetically engineered strains '705 and '706 based on strain '194 and having a knock out of gene '8676. FIG. 4b shows a bar graph illustrating average batch FAME productivity (g/m2/day) for Strain '194 versus two genetically engineered strains ('705 and '706). FIG. 4c shows a bar graph illustrating average batch TOC productivity (g/m2/day) for Strain '194 versus two genetically engineered strains ('705 and '706). FIG. 4d shows a bar graph illustrating average FAME/TOC ratio over a 5 day period for strain '194 versus two genetically engineered strains ('705 and '706).

DETAILED DESCRIPTION OF THE INVENTION

The invention provides recombinant algal mutants that have one or more genetic modification(s) to a gene encoding an RNA binding domain. The genetic modification(s) described herein result in a recombinant or mutant cell or organism having higher lipid productivity and/or higher biomass productivity. The recombinant algal mutants can also optionally have reduced chlorophyll content and/or a reduced PSII antenna size versus a corresponding control cell or organism not having the genetic modification. In various embodiments the genetic modification(s) described herein can result in substantial increases in lipid productivity and/or biomass productivity. In some embodiments the genetic modifications disclosed herein can be accumulated or "stacked" with one or more additional genetic modifications in an algal cell or organism described herein (for example, modification of a gene encoding an SGI polypeptide) to result in further increases in the biomass productivity or lipid productivity. The stacking can be performed by recapitulating one or more of the modifications in a wild-type, laboratory, or other background cell or organism. The recombinant algal cells or organisms disclosed can have one, two, three, or more than two, or more than three genetic modifications described herein, and thus can have the desirable characteristics disclosed herein.

The recombinant cell or organism of the invention having a genetic modification described herein can have higher lipid productivity (e.g. as measured by FAME) and/or higher biomass productivity than a corresponding (control) cell or organism. In some embodiments the genetic modification is an attenuation(s) of a gene encoding an RBD domain. Biomass productivity can be measured as the rate of biomass accumulation, for example as the total organic carbon (TOC) content of the respective cells or organisms. In one embodiment the lipid and/or biomass productivity is higher in batch culture, i.e. a culture where nutrients are not renewed or re-supplied to the medium during culturing, compared to a corresponding (control) cell or organism. Any of the mutant cells or organisms disclosed herein can be photosynthetic cells or organisms. Any of the recombinant (mutant) cells or organisms described herein can exhibit increased lipid productivity and/or increased biomass productivity under photoautotrophic conditions compared to a corresponding control cell or organism, i.e. conditions where the recombinant cells or organisms can produce their own biomass using light, carbon dioxide, water, and nutrients via photosynthesis. Corresponding (control) cells or organisms are cells or organisms that are useful for evaluating the effect of any one or more of the genetic modifications. Corresponding (control) cells or organisms are cells or organisms that do not have the one or more genetic modifications being evaluated and that are subjected to the same or substantially the same conditions as the test cells or organisms such that a difference in the performance or characteristics of the cells or organisms is based only on the genetic modification(s) being evaluated. In any embodiment the corresponding (control) cells or organisms can be of the same species as the test organism. They can also be the same or similar in every way except for the one or more genetic modification(s) being evaluated. In some embodiments the corresponding (control) cell or organism is a wild-type cell or organism. But the corresponding (control) cell or organism can also be a laboratory strain or parental strain of the test cell or organism. Substantially the same conditions can be the same conditions or slightly different conditions where the difference does not materially affect the function, activity, or expression of the nucleic acid sequence modified.

In one embodiment the recombinant cells or organisms are algal cells. In one embodiment the recombinant alga has a genetic modification to a gene encoding an RNA binding domain. Additionally and optionally any of the recombinant alga can further have a genetic modification described herein to a gene or nucleic acid encoding an SGI1 polypeptide.

The lipid products of these mutants can be further processed into biofuels or used in the production of other specialty chemical products. The genes encoding the RNA binding domain and the optional SGI1 polypeptide can be any of the nucleic acid sequences described herein, hereby disclosed in all possible combinations or sub-combinations as if set forth fully herein. In some embodiments the encoded SGI1 polypeptide can have a polypeptide sequence selected from any one or more of SEQ ID NOs: 5-16, or a sequence having at least 90% or at least 95% or at least 98% sequence identity to any one or more of SEQ ID NO: 5-16.

In some embodiments recombinant cells or organisms of the invention can have a reduced amount of chlorophyll b, and can have an increased chlorophyll a to chlorophyll b ratio (chl a/chl b) compared to a corresponding control cell or organism. The recombinant cells or organisms can have decreased photosynthetic antenna size, for example reduced photosystem II (PSII) and/or reduced photosystem I (PSI) antenna size. In various embodiments the cross-sectional unit size of the PSII and/or PSI antenna of the recombinant cells or organisms disclosed herein can be reduced by at least 10%, at least 20%, at least 30%, at least 25%, at least 30%, at least 35%, at least 40%, at least 45%, at least 50%, or at least 60% compared to the PSII and/or PSI antenna size of a corresponding control cell or organism. The recombinant cells or organisms can have a higher growth rate and/or a higher biomass productivity than a corresponding control cell or organism not having the genetic modification, for example, higher biomass productivity per hour or per day or per period of 2 days or 3 days or 4 days or 5 days or 6 days. "Biomass" refers to cellular mass, whether of living or dead cells. Biomass productivity, or biomass accumulation, or growth rate, can be measured by any means accepted in the art, for example as ash free dry weight (AFDW), dry weight, wet weight, or total organic carbon (TOC) productivity. In any embodiment biomass productivity, or biomass accumulation, or the growth rate, can be measured as total organic carbon (TOC) productivity.

The recombinant cells or organisms of the invention can produce a greater amount of a bioproduct per time period (e.g. per minute or per hour or per day or per period of 2 days or 3 days or 4 days or 5 days or 6 days), for example a lipid product (which can optionally be measured as FAME), a carbohydrate, a protein product, a polyketide, a terpenoid, a pigment, an antioxidant, a vitamin, one or more nucleotides, one or more nucleic acids, one or more amino acids, one or more carbohydrates, an alcohol, a hormone, a cytokine, a peptide, or a polymer than a corresponding (control) organism not having the genetic modification(s). The amount of product can be expressed as g/time period, mg/time period, ug/time period, or any other defined quantity per defined time period described herein. Such bioproducts can be isolated from a lysate or biomass or cellular secretion of any of the recombinant cells or organisms of the invention. In some embodiments, the recombinant cells or organisms of the invention produce at least 10%, at least 15%, at least 20%, at least 25%, at least 30%, at least 35%, at least 40%, at least 45%, at least 50%, at least 60%, at least 70%, at least 80%, at least 90% or at least 100% more of a bioproduct than a corresponding control alga cultured under the substantially the same conditions, which can be batch, semi-continuous, or continuous culture conditions and may be nutrient replete culture conditions or may be nitrogen deplete conditions, and may be photoautotrophic conditions.

Without wanting to be bound by any particular theory it is believed that the genetic modifications described herein result in an attenuation or elimination of expression of the RNA binding domain. Such attenuation or elimination results in a significant increase in lipid productivity in the cell, which in one embodiment can be measured as the total FAME produced by the cell. A further result can be a significant increase in biomass productivity, which in one embodiment can be demonstrated by the organic carbon produced by the cell (as measured, for example, by total organic carbon).

As used herein, "exogenous" with respect to a nucleic acid or gene indicates that the nucleic acid or gene has been introduced (e.g. "transformed") into an organism, microorganism, or cell by human intervention. For example, such an exogenous nucleic acid can be introduced into a cell or organism via a recombinant nucleic acid construct. An exogenous nucleic acid can be a sequence from one species introduced into another species, i.e., a "heterologous" nucleic acid. A heterologous nucleic acid can also be an exogenous synthetic sequence not found in the species into which it is introduced. An exogenous nucleic acid can also be a sequence that is homologous to an organism (i.e., the nucleic acid sequence occurs naturally in that species or encodes a polypeptide that occurs naturally in the host species) that has been isolated and subsequently reintroduced into cells of that organism. In some embodiments an exogenous nucleic acid that includes a homologous sequence can be distinguished from the naturally-occurring sequence by the presence of non-natural sequences linked to the exogenous nucleic acid, which can include but are not limited to non-native regulatory sequences attached to the homologous gene sequence in a recombinant nucleic acid construct. Alternatively or in addition, a stably transformed exogenous nucleic acid can be detected and/or distinguished from a native gene by its juxtaposition to sequences in the genome where it has integrated. Further, a nucleic acid is considered exogenous if it has been introduced into a progenitor of the cell, organism, or strain under consideration.

A "recombinant" or "engineered" nucleic acid molecule is a nucleic acid molecule that has been altered through human manipulation. As non-limiting examples, a recombinant nucleic acid molecule includes any nucleic acid molecule that: 1) has been partially or fully synthesized or modified in vitro, for example, using chemical or enzymatic techniques (e.g., by use of chemical nucleic acid synthesis, or by use of enzymes for the replication, polymerization, digestion (exonucleolytic or endonucleolytic), ligation, reverse transcription, transcription, base modification (including, e.g., methylation), integration or recombination (including homologous and site-specific recombination) of nucleic acid molecules); 2) includes conjoined nucleotides that are not conjoined in Nature; 3) has been engineered using molecular biology techniques such that it lacks one or more nucleotides with respect to the naturally occurring nucleic acid molecule sequence; and/or 4) has been manipulated using molecular biology techniques such that it has one or more sequence changes or rearrangements with respect to the naturally occurring nucleic acid sequence, or has a sequence (e.g. by insertion) not found in the naturally occurring nucleic acid sequence. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector.

When applied to organisms, the terms "transgenic" "transformed" or "recombinant" or "engineered" or "genetically engineered" refer to organisms that have been manipulated by introduction of an exogenous or recombinant nucleic acid sequence into the organism, or by genetic modification of native sequences (which are therefore then recombinant). Recombinant or genetically engineered organisms can also be organisms into which constructs for gene "knock down," deletion, attenuation, inactivation, or disruption have been introduced to perform the indicated manipulation. Such constructs include, but are not limited to, RNAi, microRNA, shRNA, antisense, and ribozyme constructs. A recombinant organism can also include those having an introduced exogenous regulatory sequence operably linked to an endogenous gene of the transgenic microorganism, which can enable transcription in the organism. Also included are organisms whose genomes have been altered by the activity of meganucleases or zinc finger nucleases. A heterologous or recombinant nucleic acid molecule can be integrated into a genetically engineered/recombinant organism's genome or, in other instances, not integrated into a recombinant/genetically engineered organism's genome, or can be present on a vector or other nucleic acid construct. As used herein, "recombinant microorganism" or "recombinant host cell" includes progeny or derivatives of the recombinant microorganisms of the disclosure.

Any of the recombinant algal cells or organisms described herein can be generated by human intervention, for example, by classical mutagenesis and/or genetic engineering, but can also be produced by any feasible mutagenesis method, including but not limited to exposure to UV light, CRISPR/Cas9, cre/lox, gamma irradiation, or chemical mutagenesis. Screening methods can be used to identify mutants having desirable characteristics (e.g., reduced chlorophyll and increased lipid and/or biomass productivity. Methods for generating mutants of algal organisms using classical mutagenesis, genetic engineering, and phenotype or genotype screening are well-known in the art.

Algal Cell or Organism

The recombinant algal cell or organism of the invention can be a mutant microalga, or a mutant photosynthetic organism, or a mutant green alga. The recombinant alga can be any eukaryotic microoalga such as, but not limited to, a Chlorophyte, an Ochrophyte, or a Charophyte alga. In some embodiments the mutant microalga can be a Chlorophyte alga of the taxonomic Class Chlorophyceace, or of the Class Chlorodendrophyceace, or the Class Prasinophyceace, or the Class Trebouxiophyceae, or the Class Eustigmatophyceae. In some embodiments, the mutant microalga can be a member of the Class Chlorophyceace, such as a species of any one or more of the genera *Asteromonas, Ankistrodesmus, Carteria, Chlamydomonas, Chlorococcum, Chlorogonium, Chrysosphaera, Dunaliella, Haematococcus, Monoraphidium, Neochloris, Oedogonium, Pelagomonas, Pleurococcus, Pyrobotrys, Scenedesmus,* or *Volvox*. In other embodiments the mutant microalga of the invention can be a member of the Order Chlorodendrales, or Chlorellales. In other embodiments, the mutant microalga can be a member of the Class Chlorodendrophyceae, such as a species of any one or more of the genera *Prasinocladus, Scherffelia,* or *Tetraselmis*. In further alternative embodiments, the mutant alga can be a member of the Class Prasinophyceace, optionally a species of any one or more of the genera *Ostreococcus* or *Micromonas*. Further alternatively, the mutant microalga can be a member of the Class Trebouxiophyceae, and optionally of the Order Chlorellales, and optionally a genera selected from any one or more of *Botryococcus, Chlorella, Auxenochlorella, Heveochlorella, Marinichlorella, Oocystis, Parachlorella, Pseudochlorella, Tetrachlorella, Eremosphaera, Franceia, Micractinium, Nannochloris, Picochlorum, Prototheca, Stichococcus,* or *Viridiella*, or any of all possible combinations or sub-combination of the genera. In another embodiment the recombinant alga can be a Chlorophyte alga of the Class Trebouxiophyceae and the family Coccomyxaceae, and the genus *Coccomyxa* (e.g. *Coccomyxa subelhpsoidea*). Or of the family Chlamydomonadaceae and the genus *Chlamydomonas* (e.g. *Chlamydomonas reinhardtii*); or of the family Volvocaceae and the genus *Volvox* (e.g. *Volvox carteri, Volvox aureus, Volvox globator*).

In another embodiment the recombinant alga is a Chlorophyte alga of the Class Trebouxiophyceae, or Eustigmatophyceae, and can be of the Order Chlorellales or Chlorodendrales, and can be of the Family Oocystaceae, or Chlorellaceae, or Monodopsidaceae, and optionally from a genus selected from one or more of *Oocystis, Parachlorella, Picochlorum, Nannochloropsis,* and *Tetraselmis*. The recombinant alga can also be from the genus *Oocystis*, or the genus *Parachlorella*, or the genus *Picochlorum*, or the genus *Tetraselmis*, or from any of all possible combinations and sub-combinations of the genera. In one embodiment the recombinant algal cell or organism is of the Class Trebouxiophyceae, of the Order Chlorellales, and optionally of the family Oocystaceae, and optionally can be of the genus *Oocystis*.

Genetic Modification

In various embodiments the recombinant alga of the invention can have a genetic modification to a gene encoding an RNA binding domain (RBD) or an RNA binding protein (RBP). Any of the recombinant alga of the invention can, optionally, have in addition a genetic modification to a gene encoding an SGI1 polypeptide. In one embodiment the recombinant alga of the invention has a genetic modification to a gene encoding an RNA binding protein (or RNA binding domain) and a genetic modification to a gene encoding an SGI1 polypeptide. In one embodiment each of these genetic modifications is to a native or endogenous sequence of the cell or organism.

A "genetic modification" applied in the invention can be any modification of a gene or nucleic acid sequence, e.g. any one or more of a deletion, partial deletion, a mutation, a disruption, an insertion, insertion of a stop codon, an inactivation, an attenuation, a rearrangement, one or more point mutations, a frameshift mutation, an inversion, a gene "knock out", a single nucleotide polymorphism (SNP), a truncation, a point mutation, that changes the activity or expression of the one or more gene or nucleic acids. In some embodiments the change in expression is a reduction in expression or an elimination of the expression or activity. The genetic modification can be made or be present in any sequence that affects expression or activity of the gene or nucleic acid sequence, or the nature or quantity of its product, for example to a coding or non-coding sequence, a promoter, a terminator, an exon, an intron, a 3' or 5' UTR, or other regulatory sequence; a genetic modification performed in any structure of the gene can result in attenuation or elimination of the gene or nucleic acid product or activity. In one embodiment the genetic modification is a deletion, disruption, or inactivation. In one embodiment the genetic modification is a "knock out" mutation. The genetic modification can be made to or be present in the host cell's native genome. In some embodiments, a recombinant cell or organism having attenuated expression of a gene as disclosed herein can have one or more mutations, which can be one or more nucleobase changes and/or one or more nucleobase deletions and/or one or more nucleobase insertions, into the region of a gene 5' of the transcriptional start site, such as, in non-limiting examples, within about 2 kb, within about 1.5 kb, within about 1 kb, or within about 0.5 kb of the known or putative transcriptional start site, or within about 3 kb, within about 2.5 kb, within about 2 kb, within about 1.5 kb, within about 1 kb, or within about 0.5 kb of the translational start site.

An "attenuation" is a genetic modification resulting in a reduction of the function, activity, or expression of a gene or nucleic acid sequence compared to a corresponding (control) cell or organism not having the genetic modification being examined, i.e. the diminished function, activity, or expression is due to the genetic modification. The activity of a nucleic acid sequence can be expression of an encoded product, a binding activity (e.g. RNA binding), or other activity the nucleic acid sequence exerts within the organism. In various embodiments an attenuated gene or nucleic acid sequence produces less than 90%, or less than 80%, or less than 70%, or less than 50%, or less than 30%, or less than 20%, or less than 10%, or less than 5% or less than 1% of its function, activity, or expression of the gene or nucleic acid sequence compared to the corresponding (control) cell or organism. In various embodiments a gene attenuation can be achieved via a deletion, a disruption, or an inactivation. Any of the genetic modifications described herein can result in partial or complete attenuation of the function, activity, or expression of the attenuated gene or nucleic acid sequence. Thus, deletions, functional deletions, inactivations, knock outs, and disruptions can also be attenuations. An attenuation can also be a downregulation of a gene or nucleic acid sequence, which refers to the cell or organism decreasing the amount of function, activity, or expression.

An unmodified gene or nucleic acid sequence present naturally in the organism denotes a natural, endogenous, or wild type sequence. A deletion can mean that at least part of the object nucleic acid sequence is deleted, but a deletion can also be accomplished by disrupting a gene through, for example, the insertion of a sequence into the gene (e.g. a selection marker), a combination of deletion and insertion, or mutagenesis resulting in insertion of a stop codon. But a deletion can also be performed by other genetic modifications known to those of ordinary skill that result in the loss of expression, activity, or function of a gene or nucleic acid sequence.

A functional deletion is a genetic modification that removes at least so much of the activity or expression of a gene or nucleic acid sequence that any remaining activity or expression of the gene or nucleic acid sequence has no significant effect on the cell or organism compared to a corresponding (control) cell or organism not having the functional deletion and cultivated under the same or substantially the same conditions. In some embodiments the functional deletion can remove all function, activity, or expression of the gene or nucleic acid sequence. A functional deletion can involve an at least partial deletion of the coding or non-coding sequence of the gene that removes all function, activity, or expression of an indicated gene or nucleic acid sequence. A "deletion" involves deletion of the indicated gene or nucleic acid sequence and removes all function, activity, or expression of a gene or nucleic acid sequence. A "disruption" or "knock out" of a gene is an insertion, deletion, or other sequence modification (e.g. an SNP, an inversion, or other modification) of a nucleic acid sequence of the coding, non-coding, or regulatory portion of a gene with resulting complete loss of product, expression, or activity of the gene. An "inactivation" causes loss of activity or expression of an inactivated gene or nucleic acid sequence and can be reversible or irreversible (for example the reversible or irreversible binding of a component to the gene or nucleic acid sequence). Functional expression refers to the expression of a functional product or activity of a nucleic acid sequence. When the expressed product of a nucleic acid is a polypeptide, functional expression means expression of polypeptide activity having at least 10% or at least 25% or at least 50% or at least 75% of the activity of a corresponding unmodified cell or organism. For activity of a gene or nucleic acid sequence functional expression means activity or expression of at least 10% or at least 25% or at least 50% or at least 75% of the activity or expression of a corresponding (control) cell or organism not having the modification and cultivated under the same or substantially the same conditions. Thus, various types of genetic modifications can be given terms that overlap in description. Persons of ordinary skill know that the particular term describing a genetic modification can be dependent both on how a gene or its components, or nucleic acid sequence is being physically changed as well as on the context. The recombinant cells or organisms of the invention can have any of the types of genetic modifications described herein.

In one embodiment the genetic modification is a "knock out" mutation involving the introduction of a stop codon into a gene (or regulatory sequence of the gene) or nucleic acid sequence encoding an RNA binding domain or RNA binding protein described herein and/or into a gene or nucleic acid sequence encoding an SGI1 polypeptide, as described herein. For example in one embodiment the genetic modification can be a stop mutation introduced into SEQ ID NOs: 1 or 2 (the nucleic acid sequence and coding sequence of RNA binding domain from *Oocystis* sp.) or into a variant of either, or into a nucleic acid sequence encoding the polypeptide of SEQ ID NO: 4 (RNA binding domain from *Parachlorella*), or into a variant thereof. Variant sequences have at least 60% sequence identity or at least 70% sequence identity or at least 75% or at least 80% or at least 85% or at least 90% or at least 95% or at least 98% sequence identity to any nucleic acid or polypeptide sequence of any one of SEQ ID NOs: 1-16. In one embodiment the genetic modification is a modification that results in a stop mutation (or nonsense mutation) at the sequence coding for Gln316* (Q316Stop or Q316*) inserted into SEQ ID NO: 1 or 2 or a variant of either. The genetic modification can also be targeted to a regulatory sequence with the effect of eliminating or diminishing the activity or expression of a nucleic acid sequence, for example any one or more of SEQ ID NO: 1-16 or a variant of any of them.

The genetic modification can also be a stop mutation or nonsense mutation introduced into a gene or nucleic acid sequence encoding an RNA binding domain disclosed herein. In various embodiments the gene or nucleic acid sequence is SEQ ID NO: 1 or 2 (or a variant thereof) or a gene or nucleic acid sequence encoding the polypeptide of SEQ ID NO: 4 (or a variant thereof), which stop mutation can be introduced at any location of the sequence or into a regulatory sequence governing the sequence, where the modification results in a termination of transcription from the gene prior to its natural point. Thus, in one embodiment the mutation is the introduction of a stop codon that functionally deletes or disrupts the activity or expression of the gene or nucleic acid sequence. The stop codon or other modification can also be introduced at many different loci or locations within a gene encoding an RNA binding domain, or in a regulatory sequence, for example at a promoter, terminator, or other regulatory sequence that attenuates the gene or the activity of the encoded polypeptide, and that results in functional deletion of the gene. Analogous modifications can be made to the sequence(s) for similar effect. Such insertion or deletion or other mutation can also cause a loss of function or activity in the RNA binding domain and/or SGI1 polypeptide, and result in the effect of increased lipid productivity.

Any of the recombinant cells or organisms of the invention can have a reduced functional absorption cross section of PSII and/or reduced PSII antenna size. For example, the cross-sectional unit size of the PSII antenna can be reduced by at least about 10%, at least 20%, at least 30%, at least 25%, at least 30%, at least 35%, at least 40%, at least 45%, at least 50%, at least 60%, at least about 70%, or at least about 80% compared to the functional absorption cross section of PSII and/or PSII antenna size of the corresponding (control) cell or organism not having the genetic modification. In some embodiments the recombinant cells or organisms of the invention can additionally (and optionally) have a reduced functional absorption cross section of PSI or reduced PSI antenna size by the same amounts stated above versus a corresponding (control) cell or organism.

In some embodiments, a recombinant algal cell or organism as provided herein can have increased Fv/Fm with respect to a corresponding control cell or organism. For example, the mutant photosynthetic organism may have Fv/Fm increased by at least 5%, at least 10%, at least 12%, at least 15%, at least 20%, at least 30%, at least 40% or at least 50% compared to a corresponding (control) photosynthetic organism. In various embodiments the Fv/Fm can be increased by 5-50%, or by 5-30% or by 5-20% with respect to a control photosynthetic organism.

Further, a mutant photosynthetic organism as provided herein can have an increased rate of electron transport on the acceptor side of photosystem II with respect to a control or wild type cell. The rate can be at least about 20%, 30%, 40%, 50%, 60%, 80%, or 100% higher compared to a corresponding control cell or organism. In addition, mutant photosynthetic cells or organisms of the invention can have a rate of carbon fixation (Pmax (C)) in a recombinant cell or organism as provided herein can be elevated with respect to a control organism. For example, Pmax (14C) can be increased by at least about 20%, 30%, 40%, 50%, 60%, 80%, or 100% compared to a corresponding control cell or organism.

In some embodiments, the recombinant cells or organisms of the invention have decreased PSI and/or PSII antenna size and can optionally also have a higher amount of a ribulose bisphosphate carboxylase activase (Rubisco activase or "RA") than a corresponding (control) or wild type organism, for example, at least 1.2, 1.4, 1.6, 1.8, 2, 2.2, or 2.5 fold the amount of RA as a control organism. In some embodiments, the mutants demonstrate reduced expression of 6, 8, 10, 12, or 14 LHCP genes and increased expression of an RA gene, such as an RA-a or RA-P gene. Thus, the recombinant cells or organisms of the invention can be mutant photosynthetic organisms having reduced chlorophyll and reduced PSII antenna size where the mutants have a higher amount of Rubisco activase than control photosynthetic organisms.

The LHC super-gene family encodes the light-harvesting chlorophyll a/b-binding (LHC) proteins that constitute the antenna system of the photosynthetic apparatus. A recombinant algal mutant of the invention can also have a reduced expression of one or more LHC genes. Thus, in some embodiments the recombinant cells or organisms of the invention have at least 6, at least 8, at least 10, or at least 12 LHC genes that are attenuated or downregulated with respect to their expression level in a corresponding (control) cell or organism. In various embodiments the reduction in expression of the one or more LHC genes can be a reduction of at least 20%, or at least 30%, or at least 40%, or at least 50%, or at least 60%, or at least 70% in the level of LHC transcripts compared to the control cell or organism.

The structure of a gene consists of many elements, of which the protein coding sequence is only one part. The gene includes nucleic acid sequences that are not transcribed and sequences that are untranslated regions of the RNA. Genes also contain regulatory sequences, which includes promoters, terminators, enhancers, silencers, introns, 3' and 5' UTRs, and coding sequences, as well as other sequences known to be a part of genes. In various embodiments any of these structures or nucleic acid sequences can have one or more of the genetic modifications described herein that result in the higher lipid productivity and/or higher biomass productivity as described herein.

RNA Binding Domain

RNA binding proteins (RBPs) are involved in RNA metabolism. The function of RBPs is varied and may include transient binding to RNA sequences to assist with stability, translation, splicing, regulation of alternative splicing, a component of hnRNP proteins (heterogeneous nuclear ribonucleoprotein), processing, transport, or localization. RBPs have one or more RNA binding domains (RBD) that include RNA binding motifs that recognize corresponding RNA sequences or targets. RNA recognition motifs known as RRMs comprise one family of RNA binding domains. In various embodiments the RNA binding domain that is modified in the invention can be an RRM from any one or more of the organisms described herein. In one embodiment the RNA binding domain can be an RRM superfamily protein, for example RRM_1. In other embodiments RRMs of the invention can be an RRM protein from the PFAM 0076 family. In another embodiment the RNA binding domain can comprise the RNA-1 recognition motif. It can comprise 85-95 or 80-100 or about 90 amino acids. It can also contain an eight amino acid RNP-1 consensus sequence and/or a six amino acid RNP-2 consensus sequence. The RRM can also consist of four anti-parallel beta strands and two alpha helices arranged in a beta-alpha-beta-beta-alpha-beta fold with side chains that stack with RNA bases. SEQ ID NOs: 1-2 are nucleic acid sequence that encode an RNA binding domain with three RNA Recognition Motif (RRM) domains. The RBDs of the invention having a genetic modification can have two RRM domains in the N-terminal half of the RBD and one in the C-terminal half, or at the C-terminus, of the coding sequence.

The recombinant algal cell or organism of the invention can have a genetic modification described herein to a nucleic acid sequence of SEQ ID NO: 1-2, or to a nucleic acid sequence having at least 60% sequence identity or at least 70% sequence identity or at least 75% or at least 80% or at least 85% or at least 90% or at least 95% or at least 98% sequence identity to any one of SEQ ID NOs: 1-2, or to fragments of either sequence of at least 100 or at least 150 or at least 200 or at least 250 or at least 350 or at least 500 or at least 700 or at least 1000 contiguous nucleic acids.

The recombinant algal cell or organism of the invention can have a genetic modification described herein to a nucleic acid sequence that encodes an RNA binding domain of SEQ ID NO: 3 or 4, or to a nucleic acid sequence encoding a polypeptide having at least 50% sequence identity or at least 60% sequence identity at least 70% sequence identity or at least 75% or at least 80% or at least 85% or at least 90% or at least 95% or at least 98% sequence identity to any one of SEQ ID NO: 3 or 4, or to a nucleic acid sequence encoding a polypeptide fragment having at least 100 or at least 150 or at least 200 or at least 250 or at least 300 or at least 350 or at least 500 or at least 700 or at least 1000 contiguous amino acids of SEQ ID NO: 3 or 4.

SGI1 Polypeptide

The recombinant algal cells or organisms of the invention can have a genetic modification to a nucleic acid sequence encoding an SGI1 polypeptide, as described herein. As described herein, SGI1 or "Significant Growth Improvement 1" polypeptide is a polypeptide that includes a Response Regulator receiver or "RR" domain (pfam PF00072) and a Myb-like binding domain, referred to herein simply as a "myb" domain (pfam PF00249), where the RR domain is positioned N-terminal to the myb domain or the myb domain is C-terminal to the RR domain. The amino acid sequence of an SGI1 polypeptide that encompasses the RR domain and myb domain can include a stretch of amino acids that occurs between the RR and myb domains that may be poorly conserved or not conserved among SGI1 polypeptides. The amino acid sequence occurring between the RR domain and myb domain may be referred to herein as a linker between the two domains. The linker may be of any length, and in various examples may range in length from one to about 300 amino acids, from 10 to about 200 amino acids, or from 20 to about 150 amino acids in length or from 50 to 100 amino acids. The linker region can optionally include a nuclear localization sequence (NLS).

An RR domain within an SGI1 protein can be characterized as pfam PF00072, or as a "signal receiver domain" or simply "receiver domain", and/or can be classified as cd00156 in the conserved domain database (CDD), as COG0784 in the Clusters of Orthologous Groups of proteins database, or as an Interpro "CheY-like superfamily" domain, IPRO11006. The RR domain is found in bacterial two-component regulatory systems (like the bacterial chemotaxis two-component system that includes a polypeptide known as CheY), in which it receives a signal from a sensor partner. The RR domain of such systems is often found N-terminal to a DNA binding domain and can include a phosphoacceptor site. Alignment of the RR domains of algal SGI1 attenuation mutant strains can be shown. Sub-sequences of the RR domain from *Parachlorella* sp. WT-1185, *Coccomyxa subellipsoidea*, *Ostreococcus lucimarinus*, *Chlamydomonas reinhardtii*, *Chromochloris zofingiensis*, *Volvox carteri*, *Tetraselmis* sp. 105, *Oocystis* sp. WT-4183, and *Micromonas* sp. RCC299 show substantial homology.

A myb domain within an SGI1 protein can be characterized, for example, as pfamPF00249: "Myb-like DNA-binding domain", and/or may be identified as conserved domain TIGRO1557 "myb-like DNA-binding domain, SHAQKYF class", or as an Interpro Homeobox-like domain superfamily domain (IPR009057) and/or an Interpro Myb domain (IPRO1 7930). Alignment and substantial homology was also shown of the Myb domains of algal SGI1-KO strains. Shown are sub-sequences of the Myb domains from *Parachlorella* sp. WT-1185, *Coccomyxa subellipsoidea*, *Ostreococcus lucimarinus*, *Chlamydomonas reinhardtii*, *Chromochloris zofingiensis*, *Volvox carteri*, *Tetraselmis* sp. 105, *Oocystis* sp. WT-4183, and *Micromonas* sp. RCC299.

In addition to having an RR domain N-terminal to a myb domain, an SGI1 protein as provided herein can have a score of 300 or higher, 320 or higher, 340 or higher, 350 or higher, 360 or higher, or 370 or higher with an e-value of less than about 1e-10, 1e-50, 1e-70, or 1e-100, when scanned with a Hidden Markov Model (HMM) designed to score proteins on the basis of how well a protein's amino acid sequence matches the conserved amino acids of a region of SGI1 homologs in algae. The region of SGI1 polypeptides used to develop the HMI is the amino acid sequence that includes (proceeding in the N-terminal to C-terminal direction) the RR domain, the linker, and the myb domain. In an HMM, highly conserved amino acid positions are weighted more heavily than poorly conserved amino acid positions within a compared region of the polypeptides to arrive at the score. Polypeptides having scores of at least about 300, or of 350 or greater, such as for example 370 or greater, when scanned with an HMM model based on protein sequences of algal SGI1 polypeptides that include a single continuous sequence that includes the RR domain, linker, and myb domain developed using include, without limitation, polypeptides of the algal and plant species *Parachlorella* sp. (SEQ ID NO:5), *Coccomyxa subellipsoidea* (SEQ ID NO:6), *Ostreococcus lucimarinus* (SEQ ID NO:7), *Chlamydomonas reinhardtii* (SEQ ID NO:8), *Chromochloris zofingiensis* (SEQ ID NO: 9), *Volvox carteri* (SEQ ID NO:10), *Tetraselmis* sp. 105 (SEQ ID NOs: 11-13, *Oocystis* sp. (SEQ ID NO:14), *Micromonas* sp. RCC299 (SEQ ID NO:15), and *Micromonas pusilla* (SEQ ID NO:16). Additional SGI1 orthologs from additional algae species are identifiable by persons of ordinary skill in the art.

The recombinant algal cells or organisms of the invention can further have a genetic modification to a nucleic acid sequence that encodes an SGI1 polypeptide, such as any one of SEQ ID NO: 5-16, or to a nucleic acid sequence encoding a polypeptide having at least 50%, at least 55%, at least 60%, at least 65%, at least 70%, at least 75%, at least 80%, at least 85%, at least 90%, at least 95%, at least 96%, at least 97%, at least 98%, or at least 99% amino acid sequence identity to an SGI1 polypeptide sequence of any of SEQ ID NOs: 5-16, or to fragments of any of them comprising a consecutive sequence of at least 100, or at least 125, or at least 150, or 200 or more amino acids. The polypeptide can also have an RR domain and a myb domain, and the RR domain can be N-terminal to the myb domain, where the SGI1 polypeptide is a naturally occurring polypeptide or a variant thereof. In various embodiments, the SGI1 polypeptide is a naturally-occurring polypeptide of an algal species described herein. The genetic modification to a nucleic acid sequence encoding an SGI1 polypeptide or variant as described herein can be in addition to having the described genetic modification to a gene or nucleic acid sequence encoding an RNA binding domain, as described herein.

Persons of ordinary skill know how to calculate the percent of "sequence identity" between two sequences. Any method of determining sequence identity that has acceptance by most persons of ordinary skill in the art or otherwise widely accepted in the field can be utilized to determine the sequence identity between two sequences. In one embodiment the percent of sequence identity can be determined by BLAST (Basic Local Alignment Search Tool) analysis using the algorithm employed by the programs blastp, blastn, blastx, tblastn, and tblastx (Altschul (1997), Nucleic Acids Res. 25, 3389-3402, and Karlin (1990), Proc. Natl. Acad. Sci. USA 87, 2264-2268). In one embodiment the search parameters for histogram, descriptions, alignments, expect (i.e., the statistical significance threshold for reporting matches against database sequences), cutoff, matrix, and filter (low complexity) can be at the default settings. The default scoring matrix used by blastp, blastx, tblastn, and tblastx can be the BLOSUM62 matrix (Henikoff (1992), Proc. Natl. Acad. Sci. USA 89, 10915-10919). For blastn the scoring matrix can be set by the ratios of M (i.e., the reward score for a pair of matching residues) to N (i.e., the penalty score for mismatching residues), wherein the default values for M and N can be +5 and −4, respectively. Four blastn parameters can be adjusted as follows: Q=10 (gap creation penalty); R=10 (gap extension penalty); wink=1 (generates word hits at every winkth position along the query); and gapw=16 (sets the window width within which gapped alignments are generated). The equivalent Blastp parameter settings for comparison of amino acid sequences can be: Q=9; R=2; wink=1; and gapw=32. A Bestfit comparison between sequences, available in the GCG package version 10.0, can use DNA parameters GAP=50 (gap creation penalty) and LEN=3 (gap extension penalty), and the equivalent settings in protein comparisons can be GAP=8 and LEN=2.

Increased Lipid Productivity

The recombinant mutant algae of the invention having a genetic modification to a gene or nucleic acid sequence encoding an RNA binding domain as described herein can demonstrate an increase in the production of lipid in the cell or organism versus a corresponding (control) cell or organism. The increase in lipid production can be measured by any accepted and suitable method, for example using fatty acid methyl ester (FAME) analysis. In one embodiment the increase in lipid production is measured as an increase in total FAME produced by the recombinant organisms. The recombinant cells or organisms of the invention having a genetic modification to a gene or nucleic acid encoding an RNA binding domain and, optionally, a genetic modification to a gene or nucleic acid sequence encoding SGI1 polypeptide, can exhibit at least 15% or at least 20% or at least 30% or at least 40% or at least 50% or at least 60% or at least 70% or at least 80% or at least 90% or at least 100% greater lipid productivity compared to a corresponding control cell or organism, as described herein. In other embodiments the increase in lipid productivity can be 15-25% or 15-35% or 15-45% or 15-50% or 25-45% or 25-55% or 25-70% or 25-90% or 25-100% or 25-150% or 25-200% or 30-35% or 30-45% or 30-55%. The increase can be weight for weight (w/w). In one embodiment lipid productivity is measured using the FAME profile (fatty acid methyl ester assay) of the respective cells or organisms. In one embodiment lipid productivity can be expressed as mg/L. In other embodiments the recombinant cells or organisms of the invention can exhibit at least 50 g/m2 or at least 60 or at least 70 or at least 80 grams per square meter of FAME accumulation after 5 days of cultivation. Methods of producing a FAME profile are known to persons of ordinary skill in the art. A FAME profile can be determined using any suitable and accepted method, for example a method accepted by most persons of ordinary skill in the art. The recombinant cell or organisms of the invention can, optionally, also have an increase in biomass productivity can be 15-35% or 15-40% or 25-45% or 15-50% or 25-70% or 50-100% or 50-200% (w/w).

An increase in lipid production or lipid productivity can be measured by weight, but can also be measured in grams per square meter per day of the surface of a cultivation vessel (e.g. a flask, photobioreactor, cultivation pond). In various embodiments the recombinant alga of the invention produce at least 3 or at least 4 or at least 5 or at least 6 or at least 7 or at least 8 or at least 10 or at least 12 or at least 13 or at least 14 grams per square meter per day of lipid production, which can be measured by the FAME profile. In any of the embodiments the high lipid and/or high biomass productivity phenotype can be obtained under nitrogen deplete conditions, which in some embodiments can involve dilution and/or replacement of medium with fresh nitrogen deplete medium during growth. Dilutions can be by any suitable amount, for example dilution by about 50% or by about 60% or by about 70% or at least 70%, or by about 80%, or by more than 80%. In one embodiment the lipid product is a fatty acid and/or derivative of a fatty acid. In one embodiment the fatty acids and/or derivatives of fatty acid comprise one or more species of molecules having a carbon chain between C8-C18 and/or C8-C20 and/or C8-C22 and/or C8-C24, in all possible combinations and sub-combinations. In one embodiment the growth conditions can be batch growth, involving spinning cells to remove nitrogen from the medium, replacing with nitrogen deplete medium, and resuming batch growth.

In any of the embodiments the genetic modification to the gene or nucleic acid sequence encoding an RBD domain (and/or the optional genetic modification to a gene or nucleic acid sequence encoding an SGI1 polypeptide) can result in an attenuation of expression of the respective gene(s). The genetic modification of any one or more of these genes or nucleic acids can be any of those described herein. In one embodiment the genetic modification is a deletion, disruption, or inactivation. In another embodiment the genetic modification is a deletion (which optionally, can be a functional deletion) or a disruption or knock out of the gene.

Biomass Productivity

The recombinant algal cells of the invention having a genetic modification to a gene or nucleic acid encoding an RNA binding domain described herein, and optionally, to a gene or nucleic acid sequence encoding an SGI1 polypeptide described herein, can also have higher biomass productivity than a corresponding (control) organism not having the genetic modification. Biomass can be measured using the total organic carbon (TOC) analysis, known to persons of ordinary skill in the art. The recombinant cells can have at least 20% higher or at least 25% higher or at least 30% higher or at least 35% higher, or at least 50% higher or at least 60% higher or at least 70% higher or at least 80% higher or at least 90% higher or at least 100% higher or at least 125% higher or at least 150% higher or at least 200% higher biomass productivity than a corresponding (control) cell or organism, which in one embodiment can be measured by total organic carbon analysis. In other embodiments the biomass productivity can be 15-35% or 15-40% or 25-45% or 15-50% or 25-70% or 50-100% or 50-200%.

Various methods of measuring total organic carbon are known to persons of ordinary skill in the art. Biomass productivity can be measured as mg/ml of culture per time period (e.g. 1 day or 2 days or 3 days or 4 days or 5 days). In some embodiments the higher biomass productivity and/or higher lipid productivity as described herein can occur under nitrogen deplete conditions. Thus, in one embodiment the recombinant alga of the invention can have higher lipid production and/or higher total organic carbon production than a corresponding (control) cell or organism, which higher amount can be produced under nitrogen deplete or low nitrogen conditions. Nitrogen deplete conditions can involve culturing in a buffer having less than 0.5 mM of nitrogen in any available form external to the cell or organism. In one embodiment the cells can be cultured in 0.5 mM or less of KNO3 or urea as a nitrogen source. Other buffers may also be used and be nitrogen deplete if they contain a level of nitrogen that does not change the physiology of a nitrogen-related parameter (e.g. lipid productivity or biomass productivity) by more than 10% versus culturing the cell in a medium free of a nitrogen source external to the cells or organisms. In any embodiment biomass productivity can be evaluated by measuring an increase in the total organic carbon of the cells. Nutrient replete conditions are those where the growth of the cultivated organism is not limited by a lack of any nutrient.

In various embodiments the one or more genetic modification(s) can be made in (i.e. derived from) a cell or organism that is a wild type, parent, or laboratory strain. Laboratory strains are organisms that have been cultured in a laboratory setting for a period of time sufficient for the strain to undergo some adaptation(s) advantageous to growth in the laboratory environment and render the strain distinctive versus a more recently cultured wild-type strain. Laboratory strains nevertheless can be genetically modified as described herein and yield significant desirable characteristics from the genetic modification(s), as described herein. For example, laboratory strains can have higher biomass productivity and/or higher lipid productivity than a wild-type strain. In some embodiments one or more genetic modifications disclosed herein can be performed on a laboratory strain to result in a recombinant algal organism of the invention having higher biomass productivity and/or higher lipid productivity than the laboratory strain, which higher amounts can be any of those disclosed herein. In such embodiments the laboratory strain can therefore be a corresponding control algal cell or organism described herein that does not have the genetic modification being considered.

Methods of Producing Lipid

The invention also provides methods for producing a lipid product. The methods involve culturing a recombinant algal cell or organism described herein to thereby produce a lipid product. Any of the methods can also involve a step of harvesting lipid produced by the recombinant algal cell or organism. The culturing can be for a suitable period of time, for example, at least 1 day or at least 3 days or at least 5 days.

The invention also provides methods for producing a composition containing lipids. The methods involve culturing a recombinant algal cell or organism described herein to thereby produce a composition containing lipids. The composition can be a biomass composition. The cultivating can be done in any suitable medium conducive to algal growth (e.g. an algal growth medium or any medium described herein). The methods can also involve a step of harvesting lipids from the composition or biomass containing lipids. The methods can involve a step of harvesting lipids from the recombinant cells or organisms. Any of the methods herein can also involve a step of purifying the lipid containing composition to produce a biofuel or biofuel precursor. A biofuel precursor is a composition containing lipid molecules that can be purified into a biofuel.

The invention also provides methods of producing a recombinant algal cell or organism having higher lipid productivity than a corresponding control cell or organism. The methods involve exposing algal cells or organisms to ultraviolet light to produce a recombinant cell or organism described herein that has higher lipid productivity than a corresponding control cell or organism. In one embodiment algal organisms having higher lipid productivity can be identified by contacting the recombinant cells with a stain that identifies lipids (e.g. by BODIPY dye). Optionally methods can include a step of isolating lipids from the recombinant algal organisms. The recombinant alga can be cultivated in any suitable growth media for algae, such as any of those described herein. The uv treatment can involve, for example, subjecting the culture to uv light, or gamma radiation, or both, for a suitable period of time or under a suitable uv regimen or gamma radiation regimen. Persons of ordinary skill understand suitable regimens for uv exposure for mutagenesis. The uv regimen can involve exposing the cells or organisms to uv radiation, which can be performed in batches with each batch receiving a dose. Multiple cell batches can receive different doses of energy for each batch of cells. For example 4 or 5 batches of cells can receive doses of exposure to 16-57 uJ/cm2 of energy, and exposure energy can increase with each separate batch. The cell batches can be pooled together after exposures are complete. The recombinant alga (or pooled algae) can be cultivated for at least 2 days or at least 3 days, or at least 4 days, or at least 5 days, or at least 6 days, or at least 10 days, or at least 20 days, or from 2-10 days, or from 2-20 days or from 2-25 days after exposure. The recombinant algal organisms can be any described herein.

Any of the recombinant cells or organisms of the invention can be cultivated in batch, semi-continuous, or continuous culture to produce the higher biomass productivity and/or higher lipid productivity. In some embodiments the culture medium can be nutrient replete, or nitrogen deplete (—N). In some embodiment the culturing is under photoautotrophic conditions, and under these conditions inorganic carbon (e.g., carbon dioxide or carbonate) can be the sole or substantially the sole carbon source in the culture medium.

The invention also provides a biofuel comprising a lipid product of any of the recombinant cells or organisms described herein. The biofuel is produced by purifying a lipid containing composition produced by a recombinant algal cell or organism described herein.

FAME and TOC Analysis Methods

The lipid productivity of the cells or organisms can be measured by any method accepted in the art, for example as an increase or decrease in fatty acid methyl esters comprised in the cell, i.e. FAME analysis. In some embodiments any of the recombinant algal cells or organisms of the invention can have higher biomass productivity as described herein versus corresponding control cells or organisms. In some embodiments the recombinant algal cells or organisms of the invention can have higher lipid productivity and also higher biomass productivity compared to a corresponding control cell or organism. Biomass productivity can be measured by any methods accepted in the art, for example by measuring the total organic carbon (TOC) content of a cell. Embodiments of both methods are provided in the Examples.

"FAME lipids" or "FAME" refers to lipids having acyl moieties that can be derivatized to fatty acid methyl esters, such as, for example, monoacylglycerides, diacylglycerides, triacylglycerides, wax esters, and membrane lipids such as phospholipids, galactolipids, etc. In some embodiments lipid productivity is assessed as FAME productivity in milligrams per liter (mg/L), and for algae, may be reported as grams per square meter per day (g/m2/day). In semi-continuous assays, mg/L values are converted to g/m2/day by taking into account the area of incident irradiance (the SCPA flask rack aperture of 1½ inches×3⅜", or 0.003145 m2) and the volume of the culture (550 ml). To obtain productivity values in g/m2/day, mg/L values are multiplied by the daily dilution rate (30%) and a conversion factor of 0.175. Where lipid or subcategories thereof (for example, TAG or FAME) are referred to as a percentage, the percentage is a weight percent unless indicated otherwise. The term "fatty acid product" includes free fatty acids, mono-di, or tri-glycerides, fatty aldehydes, fatty alcohols, fatty acid esters (including, but not limited to, wax esters); and hydrocarbons, including, but not limited to, alkanes and alkenes).

Embodiments

In one embodiment the invention provides a recombinant algal organism of the Class Trebouxiophyceae having a genetic modification in a gene or nucleic acid sequence encoding an RNA binding domain. The recombinant alga exhibits higher lipid productivity and/or biomass productivity versus a corresponding control algal cell not having the genetic modification. In various embodiment the Trebouxiophyceae organism can be from the family Oocystaceae or Chlorellaceae. In one embodiment the organism is of the genus *Oocystis*.

In one embodiment the invention provides a recombinant Trebouxiophyceae organism having a deletion, disruption, or inactivation in a gene or nucleic acid sequence encoding an RNA binding domain. In one embodiment the deletion, disruption, or inactivation involves the insertion of a nonsense mutation in a gene or nucleic acid sequence encoding an RNA binding domain. In one embodiment the RNA binding domain can have at least 80% or at least 90% sequence identity to SEQ ID NO: 1 or 2, or a variant of either. The recombinant alga exhibits higher lipid productivity and/or biomass productivity versus a corresponding control algal cell not having the genetic modification. The alga can be a Trebouxiophyceae organism from the family Oocystaceae, for example of the genus *Oocystis*. The increase in lipid productivity can be an increase of at least 30% w/w, or 30-50% or 30-55%. The recombinant cells or organisms can, optionally, also have an increase in biomass productivity of at least 18% or at least 20% or at least 25%, or 18-40%. Thus in one embodiment the recombinant cells or organisms have an increase in lipid productivity of 30-55% and an increase in biomass productivity of at least 20%. In another embodiment the increase in lipid productivity can be at least 18%.

In one embodiment the invention provides a recombinant Trebouxiophyceae organism having a deletion, disruption, or inactivation in a gene or nucleic acid sequence encoding an RNA binding domain. In one embodiment the deletion, disruption, or inactivation involves the insertion of a nonsense mutation in a gene or nucleic acid sequence encoding an RNA binding domain. In one embodiment the RNA binding domain can have at least 80% or at least 90% sequence identity to SEQ ID NO: 1 or 2, or a variant of either. The recombinant alga exhibits higher lipid productivity and/or biomass productivity versus a corresponding control algal cell not having the genetic modification. The alga can be a Trebouxiophyceae organism from the family Oocystaceae, for example of the genus *Oocystis*. The increase in lipid productivity can be an increase of at least 30% w/w, or 30-33% or 30-35%. The recombinant cells or organisms can, optionally, also have an increase in biomass productivity of at least 25% or at least 30% or 25-35%. In another embodiment the increase in lipid productivity can be at least 18%.

In one embodiment the invention provides a recombinant algal organism of the family Oocystaceae having a deletion, disruption, or inactivation in a gene or nucleic acid sequence encoding an RNA binding domain, which optionally can be SEQ ID NO: 1 or 2, or a variant of either. The deletion can be a functional deletion. In one embodiment the deletion, disruption, or inactivation can be a nonsense mutation in SEQ ID NO: 1 or 2, or a variant of either. In one embodiment the organism can be of the genus *Oocystis*. The recombinant alga exhibits higher lipid productivity and/or biomass productivity versus a corresponding control algal cell not having the genetic modification.

In one embodiment the invention provides a recombinant algal organism of the Class Trebouxiophyceae having a genetic modification to a gene or nucleic acid sequence encoding an RNA binding domain. In one embodiment the gene or nucleic acid sequence is that of that SEQ ID NO: 1-2, or a variant of either. The genetic modification can be a deletion (optionally a functional deletion) or disruption of the gene or nucleic acid sequence. The recombinant alga exhibits higher lipid productivity and, optionally, higher biomass productivity versus a corresponding control algal cell not having the genetic modification. In various embodiment the Trebouxiophyceae organism can be from the family Oocystaceae or Chlorellaceae. In one embodiment the organism is of the genus *Oocystis*.

Example 1

This example illustrates the mutagenesis and screening of wild-type cells. Mutagenized *Oocystis* sp. cells were acclimated to diel growth in culture flasks at a light intensity of about 100 uE and 1% CO2 in urea supplemented minimal medium for a week. The culture was scaled up for 3 days 500 mL square-bottom flasks, bubbled with 1% CO2 at a maximum irradiance of about 1400 uE under diel conditions, to an OD730 of about 1.0. The culture was then centrifuged at 5000 g for 10 mins and the cell pellets resuspended in nitrogen-free minimal medium to an OD730 of about 0.9. This nitrogen-free culture was then incubated for 48 hrs in square-bottom flasks bubbled with 1% CO2 at a maximum irradiance of ~1400 uE under diel conditions.

Strain 15 (wild-type *Oocystis* sp.) cells were mutagenized using uv light at a concentration of 2e6 cell/ml and at 22.4, 33.6, 44.8 and 56 mJ/cm2 in a UV Crosslinker apparatus. Cells had been acclimated to diel growth on urea supplemented minimal medium. Mutagenized cells were allowed to recover in the dark for 48 hours. Cultures were scaled up in low light (about 100 uE) before enrichment.

Mutagenized cells were acclimated to diel growth in culture flasks at a light intensity of about 100 uE and 1% CO2 in urea supplemented minimal medium for a week. The culture was scaled up for 3 days 500 mL square-bottom flasks, bubbled with 1% CO2 at a maximum irradiance of about 1400 uE under diel conditions, to an OD730 of about 1.0. The culture was then centrifuged at 5000 g for 10 mins and the cell pellets resuspended in nitrogen-free minimal medium to an OD730 of about 0.9. This nitrogen-free culture was then incubated for 48 hrs under the same conditions.

After 48 hours of nitrogen-free batch growth, an aliquot of cells was removed and subjected to staining with the lipid-specific dye BODIPY for 10 minutes in the dark at a final concentration of 0.2 ug/ml. Mutant cells with the highest level of BODIPY staining were enriched by fluorescence activated cell sorting (FACS). Enriched cell populations were starved for nitrogen as above and subjected to further BODIPY-based FACS enrichment. This iterative process was repeated for a total of five rounds retaining the top cells in each round. The final cells were plated on minimal medium agar plates supplemented with urea to isolate single axenic colonies.

Enriched cell populations were scaled up in tissue culture flasks in minimal medium supplemented with urea, then transitioned to nitrogen-free minimal medium. The lipid and biomass accumulation of isolated mutants were compared to the parental strain wild-type cells (Strain 15) with lipid content measured by total fatty acid methyl ester (FAME) analysis and biomass measured by total organic carbon (TOC). As shown in FIG. 1, several isolates from the screen showed an increase in accumulated FAME and TOC at 2 days in nitrogen deplete minimal medium, as well as FAME/TOC ratio—an indicator of how much fixed carbon is partitioned to lipids. This indicated that mutants with improved lipid productivity had been isolated. These strains were named as shown in FIG. 1: Strains 7434, 7436, 7560, 7689, and 7690. Proline F/2 algae food was used as the nitrogen deplete medium and was made by adding 1.3 ml PROLINE® F/2 Algae Feed Part A (Pentair Aquatic Eco-Systems, Inc., Cary, NC) and 1.3 ml 'Solution C' to a final volume of 1 liter of a solution of aquarium salts (17.5 g/L). Solution C is 38.75 g/L NaH2PO4 H2O, 758 mg/L Thiamine HCl, 3.88 mg/L vitamin B12, and 3.84 mg/L biotin. However, persons of ordinary skill in the art with reference to the present disclosure will realize that many algae foods or media can be used with the nitrogen content minimized, such as by omitting urea or available nitrates.

Example 2—Sequencing and ID

This example describes the sequencing and identification of genes of interest in the mutagenized organisms. Genomic DNA was isolated from *Oocystis* sp. strain '7436 as an example and from parental Strain 15 as a control and sequenced by generating 150 bp paired end reads. Reads were processed, mapped to the wild type (Strain 15) reference genome and analyzed by a small variants algorithm. An example of a small variants algorithm is the Freebayes polymorphism detection software, although other programs can also be successfully utilized. Analysis of single nucleotide polymorphisms (SNPs) and small insertions/deletions (InDels) revealed that Strain '7436 contained a total of 129 polymorphisms. Eighteen of these mutations were located within exons or at splice junctions and were identified as being of interest for Cas9-mediated gene deletion as they had the highest probability of altering gene function and/or activity. The remaining 111 mutations were either intergenic or present in introns of a gene. An assessment of transcriptomics data from the strains indicated that none of these 111 mutations had any significant impact on gene expression or transcript splicing.

TABLE 1

Mutations identified within exons or at splice junctions ('7436)

| | Transcripts | Descriptions | Type | Reference | Alteration | AA Mod |
|---|---|---|---|---|---|---|
| 1 | EMRE3EUKT2018676 | RNA-binding (RRM/RBD/RNP motifs) family protein isoform 3 | SNP | G | A | Gln316* |
| 2 | EMRE3EUKT2020737 | DnaJ-like protein subfamily C member 10 | SNP | T | A | Lys26* |
| 3 | EMRE3EUKT2019222 | NAD(P)-binding Rossmann-fold domains | Complex | CC | TT | Glu47Lys |
| 4 | EMRE3EUKT2015847 | alpha/beta-Hydrolases | SNP | C | T | Glu780Lys |
| 5 | EMRE3EUKT2034031 | Acetyl-/propionyl-coenzyme A carboxylase alpha chain | SNP | C | T | Glu53Lys |
| 6 | EMRE3EUKT2011369 | Mitochondrial inner membrane translocase subunit Tim17 | SNP | T | A | Leu133His |
| 7 | EMRE3EUKT2024333 | Serine/threonine-protein phosphatase 2A regulatory subunit B" subunit alpha | SNP | G | A | Pro446Ser |
| 8 | EMRE3EUKT2021201 | Iron-sulfur cluster biosynthesis family protein isoform 1 | SNP | G | A | Arg22Cys |
| 9 | EMRE3EUKT2026933 | Protein kinase-like (PK-like) | SNP | T | A | Ile56Phe |
| 10 | EMRE3EUKT2013538 | P-loop containing nucleotide triphosphate hydrolases | Complex | GT | AA | Asn187Ile |
| 11 | EMRE3EUKT2014336 | Conserved predicted protein, Retrovirus-related pol polyprotein from transposon tnt 1-94 | SNP | T | A | Glu21Asp |
| 12 | EMRE3EUKT2010628 | Potential peptidoglycan binding protein | Complex | TTA | CTG | LeuIle3ProVal |

TABLE 1 -continued

Mutations identified within exons or at splice junctions ('7436)

| | Transcripts | Descriptions | Type | Reference | Alteration | AA Mod |
|---|---|---|---|---|---|---|
| 13 | EMRE3EUKT2037087 | Conserved predicted protein | SNP | G | A | Ser59Leu |
| 14 | EMRE3EUKT2033739 | Conserved predicted protein | SNP | C | T | Arg246Lys |
| 15 | EMRE3EUKT2021455 | Conserved predicted protein | SNP | T | A | Tyr114Asn |
| 16 | EMRE3EUKT2014216 | Conserved predicted protein | SNP | C | T | Ser163Leu |
| 17 | EMRE3EUKT2022499 | Plastidic atp adp transporter | SNP | C | T | Splice junction |
| 18 | EMRE3EUKT2010783 | Thioredoxin-like | Insertion | GCACACACACGCACACACACA ACACACACACCACACACACAC ACACAC | ACACACACACCACACACACAC ACACAC | Splice junction |

Example 3

The identity of the mutation(s) that caused the high lipid phenotype in Strain '7436 was investigated by creating independent knockouts of genes bearing SNPs via RNP-based Cas9-mediated gene disruption in the Strain 15 wild-type, as well as in another background laboratory strain (194) that had been evolved from the wild type and had improved biomass and lipid productivity. To introduce the ribonucleoprotein comprised of the Cas9 and bound guide RNA, gold particles (0.6 micrometers) were coated with the Cas9 ribonucleoprotein along with a blasticidin deaminase gene expression cassette which will confer resistance to blastisidin when stably transformed into cells. The coated gold particles were bombarded into the above-mentioned strains using a Helios® Gene Gun System (Bio-Rad, Hercules, Calif., USA) according to manufacturer's instructions. The bombarded cells were allowed to recover for 24 hours and then plated on agar plates containing growth medium and blasticidin. Colonies formed due to stable expression of the blasticidin deaminase gene introduced during bombardment. These colonies were analyzed by PCR with primers targeting the desired genes, where Cas9 induced insertions and deletions which would cause a knockout of the target gene were validated. All strains generated were assayed for improved biomass and lipid accumulation during nitrogen starvation in growth flasks.

From this analysis four independent cell lines were identified having deletions in gene '8676 (SEQ ID NO: 1), which is a gene that encodes an RNA binding domain. These RBD mutant strains showed significant improvement in both biomass and lipid accumulation during nitrogen starvation relative to the parental lines. Two of these were constructed by recapitulation in the Strain 15 wild-type background (strains '0086 and 0338), while the other two were recapitulated in the Strain '194 laboratory strain (strains '0705 and '0706). The strains genetically engineered from the wild-type Strain 15 showed about a 33% and 32% improvement in 2-day FAME accumulation, and a 34% and 27% improvement in TOC accumulation relative to the wild-type, and much higher FAME/TOC ratios (FIG. 2). The strain engineered from the Strain '194 background strain (strains '0705 and '0706) showed about a 20% increase in FAME accumulation versus the background strain, and small improvements in TOC accumulation, and much higher FAME/TOC ratios (FIG. 3a).

Additional larger scale productivity testing was conducted over 5 day periods and revealed that the two lines engineered from Strain '194 (RDB mutant) showed about a 35-40% improvement in batch lipid productivity under nitrogen deplete conditions (FIG. 4a-b), confirming the results from smaller scale studies. The increase in FAME accumulation was sustained over the 5 day period and the measured FAME/TOC was also substantially higher on each day of the experiment for both engineered strains (FIG. 4d). Therefore, deletion of the RBD-encoding gene (8676) was sufficient to significantly improve lipid productivity.

Example 4

The amino acid sequence of RBD-8676 was analyzed for functional domains and orthologs in other species and found to encode an RNA binding protein (RBP) with 3 RNA Recognition Motif (RRM) domains: two in the N-terminal half and one at the C-terminus of the coding sequence. BLAST analysis revealed orthologs of RBD-8676 are broadly distributed in green algae and plants (Table 2).

TABLE 2

| | Organisms | Gene ID | % Identity | % Similarity [Positives] |
|---|---|---|---|---|
| 1 | Coccomyxa subellipsoidea | XP_005652122.1 | 57 | 78 |
| 2 | Chlamydomonas reinhardtii | PNW71638.1 | 57 | 74 |
| 3 | Volvox carteri | XP_002950826.1 | 56 | 73 |
| 4 | Auxenochlorella protothecoides | RMZ52765.1 | 56 | 71 |
| 5 | Chlorella sorokiniana | PRW55937.1 | 54 | 70 |
| 6 | Chlorella variabilis | XP_005850660.1 | 46 | 62 |
| 7 | Parachlorella WT1185 | EMRE3EUKT597938 | 36 | 54 |
| 8 | Picochlorum | EMRE3EUKT3376679 | 35 | 53 |
| 9 | Tetraselmis | EMRE3EUKT624082 | 36 | 52 |
| 10 | Ostreococcus lucimarinus | XP_001416933.1 | 34 | 49 |
| 11 | Arabidopsis thaliana | AT4G36960 | 45 | 68 |

What is claimed is:

1. A recombinant algal organism comprising a genetic modification in a gene encoding
   a) an RNA binding domain and comprising a nucleotide sequence having at least 90% sequence identity to SEQ ID NO: 1 or SEQ ID NO: 2, or
   b) an RNA binding domain comprising a polypeptide sequence with at least 90% sequence identity to SEQ ID NO: 3 or SEQ ID NO: 4, and
   wherein the recombinant algal organism exhibits higher lipid productivity versus a corresponding control algal organism not having the genetic modification.

2. The recombinant algal organism of claim 1, wherein the organism is a Chlorophyte alga.

3. The recombinant algal organism of claim 2, wherein the organism is of the Class Trebouxiophyceae.

4. The recombinant algal of claim 1, wherein the gene encodes an RNA binding domain comprising a sequence with at least 90% sequence identity to SEQ ID NO: 2, or the gene encodes an RNA binding domain having a polypeptide sequence with at least 90% sequence identity to SEQ ID NO: 3.

5. The recombinant algal organism of claim 3, wherein the genetic modification is a disruption.

6. The recombinant algal organism of claim 3, wherein the genetic modification results in an attenuation in expression of the encoded RNA binding domain.

7. The recombinant algal organism of claim 6, wherein the genetic modification is to a regulatory sequence of the gene encoding the RNA binding domain.

8. The recombinant algal organism of claim 7, wherein the regulatory sequence is a promoter.

9. The recombinant algal organism of claim 8, wherein the genetic modification comprises a disruption of the promoter.

10. The recombinant algal organism of claim 3, wherein the genetic modification results in the deletion of at least one amino acid in the encoded RNA binding domain sequence.

11. The recombinant alga of claim 3, wherein the genetic modification of the nucleic acid sequence encoding the RNA binding domain comprises insertion of a stop codon in the nucleic acid sequence encoding the RNA binding domain.

12. The recombinant alga of claim 1, wherein the genetic modification is a deletion, a disruption, or an inactivation in the nucleic acid sequence encoding the RNA binding domain.

13. The recombinant alga of claim 1, wherein the recombinant alga has at least 30% higher lipid productivity versus a control algae.

14. The recombinant alga of claim 13, wherein the recombinant alga has at least 50% higher lipid productivity versus a control algae.

15. The recombinant alga of claim 1, wherein the recombinant alga exhibits at least 12 grams per square meter per day of lipid production.

16. The recombinant alga of claim 1, wherein the recombinant alga further has higher biomass productivity per unit time versus the corresponding control algal cell or organism.

17. The recombinant alga of claim 16, wherein the recombinant alga has higher biomass productivity under nitrogen deficient conditions.

18. The recombinant alga of claim 1, wherein the recombinant alga has higher total organic carbon production under nitrogen deficient conditions.

19. The recombinant alga of claim 3, wherein the recombinant alga is of a family selected from the group consisting of: Oocystaceae, Chlorellaceae, and Eustigmatophyceae.

20. The recombinant alga of claim 3, wherein the recombinant alga is of a genus selected from the group consisting of: *Chlorella, Parachlorella, Picochlorum, Tetraselmis*, and *Oocystis*.

21. The recombinant algal organism of claim 3, further comprising a genetic modification to a gene encoding an SGI1 polypeptide.

22. The recombinant algal organism of claim 21, wherein the SGI1 polypeptide has at least 90% sequence identity to SEQ ID NO: 14.

23. The recombinant alga of claim 20, wherein the recombinant alga is an alga of the genus *Oocystis*.

24. A biomass product comprising the recombinant alga of claim 1.

25. A method of producing a composition containing lipids by cultivating the recombinant algal organism of claim 1 and thereby producing a composition containing lipids.

* * * * *

SEQUENCE LISTING

<160> NUMBER OF SEQ ID NOS: 16

<210> SEQ ID NO 1
<211> LENGTH: 2907
<212> TYPE: DNA
<213> ORGANISM: Oocystis sp.
<220> FEATURE:
<221> NAME/KEY: misc_feature
<223> OTHER INFORMATION: RNA Binding Domain, EMRE3EUKG2018676
      364645..367551

<400> SEQUENCE: 1

```
atggaggtcg ctacaaacgg cgaccacgcg cagcaccacc tcggcatgcc gcacggcgcg     60
cggtctgaat acagcagtgg cagcgatatg tcgcgcggcg gcggtcatgc gggcagcagc    120
ggcggccagg ctcagcagca gcaggctcag caggccgccg cagctggcga ggccggccca    180
ccgcgcaagc tggtgatcct tggcctgcca tattttacaa gcgacgacac tctgcatggc    240 tactttctc agcttggtca ggtagaggag gcgctggtca tgcgtgatca cgcgtcgggt     300
cgctcccgtg ggttcggatt tgtgacgttt attaccgccg aagacgctgc gcgcgtggct    360
gggcgggagt acagcgtcga tggtcggcga tgcgaggcaa agttcgcgct gccgcgtggc    420
gagagcgcaa gccagcgtgt tacgcgcatc ttcgtggcaa agttgccacc gcacgttgcc    480
gaggacgagc tgcgcaccta ctttgagcag gtgcgacgcc ccctgggcgct gggttccaac    540 aactgcccta gcaccggtca aaggtgcct ttaggcttct gcaggaatgt gcctccggtt     600
aatgtattga ttcatcaacc ttatcagcgt attggtgctg cattcaagtg gtgatcacca    660
cgtgcatctg ccagctgtct ctcgatcacg tctccaaacg gcgatccgcc tagtccgccc    720
aagccctgcc caagcgcgtc gtcgtgctgg gccccccgtt ccgtgtgcaa gacggtgtgc    780
ttgcttacga ggtgtatacc gttttattt cttacgcgc agtacggagc gattcaggat     840
gtgtacatgc ccaaggatgc ttccaagcag gcgcgacgtg ggattgggtt cgtgacgttc    900
gcgagccccg aggcggttga cgccgtcatt cgcacatccc acgtgttaca cggccaggag    960
ctcgtcgtcg ataaggccgc gccaaagcag aaagagccgt tccgcttggg agctggccta   1020
ccaggcgcca cagccagtgg cgtgccttac cggtcggcgc agccgtcgct gtcagccgaa   1080
cggcttgcca gcttgagcaa cggcgcattc gccggcttga ttcccggcgg ctacggcttc   1140
ggcggtcatg ggctgcagca gcagcagcac atactgccgg ggtcaatggc tggtggcgcg   1200
ctcagcggtt ctgcaggatc gctatacgac tcgttcggag gcgcgatcaa cggtactcaa   1260
gaagacggaa acggagacat gggcctttcc ggtaagcact gcttttttgc gtgcaatcta   1320
gataaaggga tatttacgtt catccatact tgtattcgca cccaggaaaa tccaggcagt   1380
tgcctgatct cacgtatttt tggtgcacgc cacgccccaa gtggaaagga ctatggaatt   1440
attaaagagt ctgcgcagaa cagacgctag ttccttcggt tctgtcagac cctacacttg   1500
ctttgctgca cgccacgccc caatcaacgt atccccctcg gtgtgcactg cgctgcccgt   1560
ttccttgcgc aggtctggga tttgtggacc acaacgcaaa cggtggcctg cacggtctgc   1620
acggcttgca aggatccaac ccaggcatgc agtatgctat tgcacagctg gcccgtgcgc   1680
agcaggcggc gcagcttggt acgtgccgcc gctgctgaac ctcaacccgc ctcccacttc   1740
atcacgctcc gttcttattg cttctttgtg cctagtatat cccatgcctc gatggcgtct   1800
cgcagtcaat aacccacaca ccaacacact aacgaattct gcatcacttg tgcggcaggt   1860
ctctcgctga catttgacgg tcgcccaagc agctccctca acctgggcgc agctgcgacg   1920
gccgcggccg cacagaatgg cggccggccg gcgggcgcgc cggcagcgc caactcgctc   1980
```

-continued

```
acagacctcg accggatgta tggcgtgcag cagcagcagc aagcaggtgc gtgtggcgtt    2040
ctgcccagct tggctggaat tattgcgcga aaggacgttc tattgatgtt ctagacaaat    2100
gacctgggtt ggaactatct cgttttttt ttaacgtgac caagaggcct gtcgtgccag     2160
gaattgctag cgagcatggt ttgagcacga gcgcgtacgc tcaccgcagt tcctcgctca    2220
gtccagccgc ctgggtttgt acgtggcctc tgcatcgttt gagcgctgca tcctcctgct    2280
ccgttgctca ccccacctcg ccccaccca ccccctgcag ggctttccac tggcctgccc     2340
aacggcctgg tctcgctgcg cggcacaggc gcaggcggcc cgaccagccc cggtggtgga    2400
cgcggccctg gcggcattgg cgctgagccg gtcgccgcag gtggtaccag tgctggcgcc    2460
ggcggggcac tgtgcaccaa ccgcgtgttc attggcaagc tgggcaagga tgtgatggag    2520
gcggacatta aggagtactg ctcgcgattt gggtacgtgc tggacgtgta catcccgcgc    2580
gacaaaaaca caagcgaga gcatcgcggc tttggctttg tgaccttcga gaccgaggcc     2640
gcggtcgatc gcatccttgc gtttgatgac caccaaatcc acggctcggt gattgccgtc    2700
gaccgagcgc tgccgaggca ggaggacacg agccagagca gcgtggcgct cagtggtgac    2760
cagcagtatg cgctgacgt cagcagtgac gctgtcagcg ccgcactcgg gatggccgcg     2820
cttggcctgg gcgccaacgg acaggtgctg ccggggcctg cgcgccacaa caacgaccgc    2880
aaccggtatc tgtaccagcc ctactag                                        2907
```

```
<210> SEQ ID NO 2
<211> LENGTH: 1860
<212> TYPE: DNA
<213> ORGANISM: Oocystis sp.
<220> FEATURE:
<221> NAME/KEY: misc_feature
<223> OTHER INFORMATION: coding sequence for RNA binding domain,
      EMRE3EUKT2018676 RNA-binding (RRM,RBD,RNP motifs) family protein
      isoform 3

<400> SEQUENCE: 2
```

```
atggaggtcg ctacaaacgg cgaccacgcg cagcaccacc tcggcatgcc gcacggcgcg    60
cggtctgaat acagcagtgg cagcgatatg tcgcgcggcg gcggtcatgc gggcagcagc    120
ggcggccagg ctcagcagca gcaggctcag caggccgccg cagctggcga ggccggccca    180
ccgcgcaagc tggtgatcct tggcctgcca tattttacaa gcgacgacac tctgcatggc    240 tactttctc agcttggtca ggtagaggag gcgctggtca tgcgtgatca cgcgtcgggt     300
cgctcccgtg ggttcggatt tgtgacgttt attaccgccg aagacgctgc gcgcgtggct    360
gggcgggagt acagcgtcga tggtcggcga tgcgaggcaa agttcgcgct ccgcgtggc     420 gagagcgcaa gccagcgtgt tacgcgcatc ttcgtggcaa agttgccacc gcacgttgcc    480
gaggacgagc tgcgcaccta ctttgagcag tacggagcga ttcaggatgt gtacatgccc    540
aaggatgctt ccaagcaggc gcgacgtggg attgggttcg tgacgttcgc gagccccgag    600
gcggttgacg ccgtcattcg cacatcccac gtgttacacg gccaggagct cgtcgtcgat    660
aaggccgcgc caaagcagaa agagccgttt ccgcttggag ctggcctacc aggcgccaca    720
gccagtggcg tgccttaccg gtcggcgcag ccgtcgctgt cagccgaacg gcttgccagc    780
ttgagcaacg gcgcattcgc cggcttgatt cccggcggct acggcttcgg cggtcatggg    840
ctgcagcagc agcagcacat actgccgggg tcaatggctg tggcgcgct cagcggttct     900 gcaggatcgc tatacgactc gttcggaggc gcgatcaacg gtactcaaga agacggaaac    960
ggagacatgg gccttttccgg tctgggattt gtggaccaca acgcaaacgg tggcctgcac   1020
```

```
ggtctgcacg gcttgcaagg atccaaccca ggcatgcagt atgctattgc acagctggcc    1080
cgtgcgcagc aggcggcgca gcttggtctc tcgctgacat ttgacggtcg cccaagcagc    1140
tccctcaacc tgggcgcagc tgcgacggcc gcggccgcac agaatggcgg ccggccggcg    1200
ggcgcgccgg gcagcgccaa ctcgctcaca gacctcgacc ggatgtatgg cgtgcagcag    1260
cagcagcaag cagggctttc cactggcctg cccaacggcc tggtctcgct gcgcggcaca    1320
ggcgcaggcg gccgaccag ccccggtggt ggacgcggcc ctggcggcat ggcgctgag    1380 ccggtcgccg caggtggtac cagtgctggc gccggcgggg cactgtgcac caaccgcgtg    1440
ttcattggca agctgggcaa ggatgtgatg gaggcggaca ttaaggagta ctgctcgcga    1500
tttgggtacg tgctggacgt gtacatcccg cgcgacaaaa acaacaagcg agagcatcgc    1560
ggctttggct ttgtgacctt cgagaccgag gccgcggtcg atcgcatcct tgcgtttgat    1620
gaccaccaaa tccacggctc ggtgattgcc gtcgaccgag cgctgccgag gcaggaggac    1680
acgagccaga gcagcgtggc gctcagtggt gaccagcagt atggcgctga cgtcagcagt    1740
gacgctgtca gcgccgcact cgggatggcc gcgcttggcc tgggcgccaa cggacaggtg    1800
ctgccggggc ctgcgcgcca caacaacgac cgcaaccggt atctgtacca gccctactag    1860

<210> SEQ ID NO 3
<211> LENGTH: 619
<212> TYPE: PRT
<213> ORGANISM: Oocystis sp.
<220> FEATURE:
<221> NAME/KEY: misc_feature
<223> OTHER INFORMATION: RNA binding domain, EMRE3EUKT2018676
      RNA-binding (RRM,RBD,RNP motifs) family protein isoform 3

<400> SEQUENCE: 3

Met Glu Val Ala Thr Asn Gly Asp His Ala Gln His Leu Gly Met
1               5                   10                  15

Pro His Gly Ala Arg Ser Glu Tyr Ser Ser Gly Ser Asp Met Ser Arg
                20                  25                  30

Gly Gly Gly His Ala Gly Ser Ser Gly Gly Gln Ala Gln Gln Gln
        35                  40                  45

Ala Gln Gln Ala Ala Ala Ala Gly Glu Ala Gly Pro Pro Arg Lys Leu
    50                  55                  60

Val Ile Leu Gly Leu Pro Tyr Phe Thr Ser Asp Asp Thr Leu His Gly
65              70                  75                  80

Tyr Phe Ser Gln Leu Gly Gln Val Glu Glu Ala Leu Val Met Arg Asp
                85                  90                  95

His Ala Ser Gly Arg Ser Arg Gly Phe Gly Phe Val Thr Phe Ile Thr
            100                 105                 110

Ala Glu Asp Ala Ala Arg Val Ala Gly Arg Glu Tyr Ser Val Asp Gly
        115                 120                 125

Arg Arg Cys Glu Ala Lys Phe Ala Leu Pro Arg Gly Glu Ser Ala Ser
    130                 135                 140

Gln Arg Val Thr Arg Ile Phe Val Ala Lys Leu Pro Pro His Val Ala
145             150                 155                 160

Glu Asp Glu Leu Arg Thr Tyr Phe Glu Gln Tyr Gly Ala Ile Gln Asp
                165                 170                 175

Val Tyr Met Pro Lys Asp Ala Ser Lys Gln Ala Arg Arg Gly Ile Gly
            180                 185                 190

Phe Val Thr Phe Ala Ser Pro Glu Ala Val Asp Ala Val Ile Arg Thr
        195                 200                 205
```

```
Ser His Val Leu His Gly Gln Glu Leu Val Asp Lys Ala Ala Pro
210                 215                 220
Lys Gln Lys Glu Pro Phe Pro Leu Gly Ala Gly Leu Pro Gly Ala Thr
225                 230                 235                 240
Ala Ser Gly Val Pro Tyr Arg Ser Ala Gln Pro Ser Leu Ser Ala Glu
            245                 250                 255
Arg Leu Ala Ser Leu Ser Asn Gly Ala Phe Ala Gly Leu Ile Pro Gly
                260                 265                 270
Gly Tyr Gly Phe Gly Gly His Gly Leu Gln Gln Gln His Ile Leu
        275                 280                 285
Pro Gly Ser Met Ala Gly Ala Leu Ser Gly Ser Ala Gly Ser Leu
290                 295                 300
Tyr Asp Ser Phe Gly Gly Ala Ile Asn Gly Thr Gln Glu Asp Gly Asn
305                 310                 315                 320
Gly Asp Met Gly Leu Ser Gly Leu Gly Phe Val Asp His Asn Ala Asn
                325                 330                 335
Gly Gly Leu His Gly Leu His Gly Leu Gln Gly Ser Asn Pro Gly Met
                340                 345                 350
Gln Tyr Ala Ile Ala Gln Leu Ala Arg Ala Gln Gln Ala Ala Gln Leu
        355                 360                 365
Gly Leu Ser Leu Thr Phe Asp Gly Arg Pro Ser Ser Ser Leu Asn Leu
370                 375                 380
Gly Ala Ala Ala Thr Ala Ala Ala Gln Asn Gly Gly Arg Pro Ala
385                 390                 395                 400
Gly Ala Pro Gly Ser Ala Asn Ser Leu Thr Asp Leu Asp Arg Met Tyr
                405                 410                 415
Gly Val Gln Gln Gln Gln Ala Gly Leu Ser Thr Gly Leu Pro Asn
                420                 425                 430
Gly Leu Val Ser Leu Arg Gly Thr Gly Ala Gly Gly Pro Thr Ser Pro
            435                 440                 445
Gly Gly Gly Arg Gly Pro Gly Gly Ile Gly Ala Glu Pro Val Ala Ala
450                 455                 460
Gly Gly Thr Ser Ala Gly Ala Gly Gly Ala Leu Cys Thr Asn Arg Val
465                 470                 475                 480
Phe Ile Gly Lys Leu Gly Lys Asp Val Met Glu Ala Asp Ile Lys Glu
            485                 490                 495
Tyr Cys Ser Arg Phe Gly Tyr Val Leu Asp Val Tyr Ile Pro Arg Asp
                500                 505                 510
Lys Asn Asn Lys Arg Glu His Arg Gly Phe Gly Phe Val Thr Phe Glu
            515                 520                 525
Thr Glu Ala Ala Val Asp Arg Ile Leu Ala Phe Asp Asp His Gln Ile
530                 535                 540
His Gly Ser Val Ile Ala Val Asp Arg Ala Leu Pro Arg Gln Glu Asp
545                 550                 555                 560
Thr Ser Gln Ser Ser Val Ala Leu Ser Gly Asp Gln Gln Tyr Gly Ala
            565                 570                 575
Asp Val Ser Ser Asp Ala Val Ser Ala Ala Leu Gly Met Ala Ala Leu
                580                 585                 590
Gly Leu Gly Ala Asn Gly Gln Val Leu Pro Gly Pro Ala Arg His Asn
            595                 600                 605
Asn Asp Arg Asn Arg Tyr Leu Tyr Gln Pro Tyr
610                 615
```

```
<210> SEQ ID NO 4
<211> LENGTH: 351
<212> TYPE: PRT
<213> ORGANISM: Parachlorella sp.
<220> FEATURE:
<221> NAME/KEY: misc_feature
<223> OTHER INFORMATION: RNA binding domain

<400> SEQUENCE: 4

Met Ser Ser Glu Glu Ile Ser Lys Asp Met Glu Ala Ser Ser Ser
1               5                   10                  15

Gly Asp Gly Gly Gly Lys Leu Phe Leu Gly Gly Leu Ser Trp Asp Thr
            20                  25                  30

Thr Glu Glu Lys Leu Arg Glu His Phe Gly Val Tyr Gly Asp Ile His
        35                  40                  45

Glu Ala Val Val Met Lys Asp Arg Thr Thr Gly Arg Pro Arg Gly Phe
    50                  55                  60

Gly Phe Val Thr Phe Lys Asp Ala Glu Val Ala Asp Arg Val Val Gln
65                  70                  75                  80

Asp Ile His Val Ile Asp Gly Arg Gln Ile Asp Ala Lys Lys Ser Val
                85                  90                  95

Pro Gln Glu Gln Lys Pro Lys Ala Arg Lys Ile Phe Val Gly Gly Leu
            100                 105                 110

Ala Pro Glu Thr Thr Glu Ala Asp Phe Lys Glu Tyr Phe Glu Arg Tyr
        115                 120                 125

Gly Ser Ile Ser Asp Val Gln Ile Met Gln Asp His Met Thr Gly Arg
    130                 135                 140

Ser Arg Gly Phe Gly Phe Ile Thr Phe Glu Glu Asp Ala Ala Val Glu
145                 150                 155                 160

Lys Val Phe Ala Gln Gly Ala Met Gln Glu Leu Gly Gly Lys Arg Ile
                165                 170                 175

Glu Ile Lys His Ala Thr Pro Lys Gly Ser Ser Pro Thr Thr Pro
            180                 185                 190

Gly Gly Arg Ser Ser Ser Gly Gly Arg Gly Gln Gly Tyr Gly Arg Ala
        195                 200                 205

Met Pro Met Pro Phe Gly Gln Leu Ala Gly Ser Pro Tyr Gly Tyr Gly
    210                 215                 220

Leu Phe His Phe Pro Pro Gly Val Met Pro His Ala Thr Pro Tyr Ser
225                 230                 235                 240

Met Gly Tyr Ala Asn Pro Tyr Leu Met Met Gln Gln Ile Ser Gly Tyr
                245                 250                 255

Pro Gly Ala Thr Pro Tyr Pro Phe Ala Gly Leu Tyr Gly Gly Gln Gly
            260                 265                 270

Arg Gly Ala Ser Gln Gln Leu Gln Gln Ala Gln His Thr Ser Gln Gln
        275                 280                 285

Leu Ser Ser Ser Gly Ala Gly Pro Val Thr Arg Leu Gln Gly Gln Gln
    290                 295                 300

Gln Gln Met Pro Gly Gln Gly Ser Arg Gln Gln His Pro Gln Ala Pro
305                 310                 315                 320

Tyr Pro Arg Pro Leu Ala Gly Ser Gly Arg Gly Lys Gly Lys Val Asp
                325                 330                 335

Ser Ala Ser Glu Leu Ser Asn His His His Ser Ala Ala His Ser
            340                 345                 350

<210> SEQ ID NO 5
```

<211> LENGTH: 619
<212> TYPE: PRT
<213> ORGANISM: Parachlorella sp.
<220> FEATURE:
<221> NAME/KEY: misc_feature
<223> OTHER INFORMATION: SGI1 polypeptide

<400> SEQUENCE: 5

```
Met Ser Gly Ser Ala Gly Ser Gly Gln Ala Thr Leu Arg His Asp Gly
1               5                   10                  15

Gly Ser Ala Gly Gly Ser Gly Pro Val Ser Asp Gly Phe Ser Pro Ala
            20                  25                  30

Gly Leu Lys Val Leu Val Val Asp Asp Asp Leu Met Cys Leu Lys Val
        35                  40                  45

Val Ser Ala Met Leu Lys Arg Cys Ser Tyr Gln Val Ala Thr Cys Ser
    50                  55                  60

Ser Gly Ser Glu Ala Leu Thr Leu Leu Arg Glu Arg Asn Glu Asp Gly
65                  70                  75                  80

Ser Ser Asp Gln Phe Asp Leu Val Leu Ser Asp Val Tyr Met Pro Asp
                85                  90                  95

Met Asp Gly Phe Lys Leu Leu Glu His Ile Gly Leu Glu Leu Glu Leu
            100                 105                 110

Pro Val Ile Met Met Ser Ser Asn Gly Asp Thr Asn Val Val Leu Arg
        115                 120                 125

Gly Val Thr His Gly Ala Val Asp Phe Leu Ile Lys Pro Val Arg Ile
    130                 135                 140

Glu Glu Leu Arg Asn Val Trp Gln His Val Val Arg Arg Arg Ser Met
145                 150                 155                 160

Ala Leu Ala Arg Thr Pro Asp Glu Gly Gly His Ser Asp Glu Asp Ser
                165                 170                 175

Gln Arg His Ser Val Lys Arg Lys Glu Ser Glu Gln Ser Pro Leu Gln
            180                 185                 190

Leu Ser Thr Glu Gln Gly Gly Asn Lys Lys Pro Arg Val Val Trp Ser
        195                 200                 205

Val Glu Met His Gln Gln Phe Val Asn Ala Val Asn Ser Leu Gly Ile
    210                 215                 220

Asp Lys Ala Val Pro Lys Arg Ile Leu Asp Leu Met Asn Val Glu Gly
225                 230                 235                 240

Leu Thr Arg Glu Asn Val Ala Ser His Leu Gln Lys Tyr Arg Leu Tyr
                245                 250                 255

Leu Lys Arg Val Glu Gly Val Gln Ser Gly Ala Ala Ala Ser Lys Gln
            260                 265                 270

His Gln His Pro Gln Tyr His Gln Gln Gln Gln Gln Gln Gln Ala Gln
        275                 280                 285

Pro Arg Ala Ala Val Ser Pro Ala Ala Ser Phe Gly Ala Leu Ser
    290                 295                 300

Leu Gly Ala Pro Gln Gln Ala Gln Gln Gly Met Pro Gln Leu Gly Met
305                 310                 315                 320

Pro Val Gln Gly Leu Pro Pro Asn Leu Ala Ala Met Gly Ser Gln Pro
                325                 330                 335

Pro His Ile Pro Phe Gln Gln Ala Leu Ala Met Gln Ala Ala Ala
            340                 345                 350

Ala Ala Ala Ala Ser Gly Ala Leu Pro Gly Ser Leu Pro Pro Tyr Met
        355                 360                 365

Pro Pro Pro Gly Met Met Pro Pro Gly Met Pro Gly Gly Val Pro Gly
```

```
                   370                 375                 380
Met Gly Gly Val Val Gly His Pro Gln Met Pro Ala Pro Gly Met Asp
385                 390                 395                 400

Phe Ala Gly Phe Asn Gly Tyr Gly Asn Ala Ala Gly Gly Leu Met Phe
                405                 410                 415

Gly Gly Gln Gln Gln Ala Gln His Ala Gln Gln His Ala Ser Ala Gln
                420                 425                 430

Ala Gly Ser Leu Ala Gln Gln Ala Gln Gln Val Ser Met Gly Leu
            435                 440                 445

Gly Leu Met Pro Pro Pro Leu Gly Phe Pro Pro Thr Ser Leu Ala Ala
            450                 455                 460

Pro Ala Pro Arg Ser Ala Ala Thr Glu Pro Ala Ala Ala Pro Leu Pro
465                 470                 475                 480

Leu Thr Ser Ser Pro Ala Ala Ser Ala Gly Gly Ser Gly Gly Pro
                485                 490                 495

Ala Ala Ala Ala Pro Gln His Ser Ser Gly Ala Ala Ala Gln Ala
                500                 505                 510

Pro His His His Pro Gln Cys Ser Glu Gln Gly Ala Gly Gly Leu Pro
            515                 520                 525

Pro Pro Leu Pro Ala Ser Ser Ala Pro Gln Ser Tyr Pro Leu Pro Pro
            530                 535                 540

Pro Ser Ser Gln Ala Ala Leu His Asp Pro Asp Glu His Tyr Pro Pro
545                 550                 555                 560

Gly Ser Ala Glu Met His His Gln His Leu Pro Gly Leu Cys Gly Phe
                565                 570                 575

Asn Pro Asp Asp Leu Leu Gly Gly Gln Leu Gly Asp Met Gly Phe Leu
                580                 585                 590

Gly Glu Leu Gly Gly Ala Val Gly Gly Lys His Glu Gln Asp Asp Phe
            595                 600                 605

Leu Asp Leu Leu Leu Lys Gly Glu Glu Glu Leu
    610                 615

<210> SEQ ID NO 6
<211> LENGTH: 302
<212> TYPE: PRT
<213> ORGANISM: Coccomyxa subellipsoidea
<220> FEATURE:
<221> NAME/KEY: misc_feature
<223> OTHER INFORMATION: SGI1 polypeptide

<400> SEQUENCE: 6

Met Gly Leu Lys Ala Arg Ala Ala Ser Val Ser Val His Ser Ser Ala
1               5                   10                  15

Asn Asn Thr Ala Ser Pro Leu Ser Gly Arg Arg Gly Phe Pro His
            20                  25                  30

Ser Gly Glu Met Ser Gly Glu Asp Leu Ala Arg Ser Asp Ser Trp Glu
        35                  40                  45

Met Phe Pro Ala Gly Leu Lys Val Leu Val Asp Asp Asp Pro Leu
    50                  55                  60

Cys Leu Lys Val Val Glu His Met Leu Arg Arg Cys Asn Tyr Gln Val
65                  70                  75                  80

Thr Thr Cys Pro Asn Gly Lys Ala Ala Leu Glu Lys Leu Arg Asp Arg
                85                  90                  95

Ser Val His Phe Asp Leu Val Leu Ser Asp Val Tyr Met Pro Asp Met
            100                 105                 110
```

```
Asp Gly Phe Lys Leu Leu Glu His Ile Gly Leu Glu Leu Asp Leu Pro
            115                 120                 125

Val Ile Met Met Ser Ser Asn Gly Glu Thr Asn Val Val Leu Arg Gly
    130                 135                 140

Val Thr His Gly Ala Val Asp Phe Leu Ile Lys Pro Val Arg Val Glu
145                 150                 155                 160

Glu Leu Arg Asn Val Trp Gln His Val Val Arg Arg Lys Arg Asp Gln
                165                 170                 175

Ala Val Ser Gln Ala Arg Asp Ser Arg Asp Ile Ser Asp Glu Glu Gly
            180                 185                 190

Thr Asp Asp Gly Lys Pro Arg Asp Lys Lys Arg Lys Glu Val Ile Leu
        195                 200                 205

Val Leu Trp Trp Asp Met Gln Arg Arg Asp Ser Asp Asp Gly Val Ser
    210                 215                 220

Ala Lys Lys Ala Arg Val Val Trp Ser Val Glu Met His Gln Gln Phe
225                 230                 235                 240

Val Gln Ala Val Asn Gln Leu Gly Ile Asp Lys Ala Val Pro Lys Arg
                245                 250                 255

Ile Leu Asp Leu Met Asn Val Asp Gly Leu Thr Arg Glu Asn Val Ala
            260                 265                 270

Ser His Leu Gln Val Pro His Leu Ser Ile Phe Ser Pro Leu Phe Ala
        275                 280                 285

Glu Leu Met Ser Thr Leu Pro Arg Arg Cys Phe Tyr Asp Phe
    290                 295                 300

<210> SEQ ID NO 7
<211> LENGTH: 270
<212> TYPE: PRT
<213> ORGANISM: Ostreococcus lucimarinus
<220> FEATURE:
<221> NAME/KEY: misc_feature
<223> OTHER INFORMATION: SGI1 polypeptide

<400> SEQUENCE: 7

Phe Pro Ala Gly Leu Gly Val Leu Val Val Asp Asp Asp Leu Leu Cys
1               5                   10                  15

Leu Lys Val Val Glu Lys Met Leu Lys Ala Cys Lys Tyr Lys Val Thr
                20                  25                  30

Ala Cys Ser Thr Ala Lys Thr Ala Leu Glu Ile Leu Arg Thr Arg Lys
            35                  40                  45

Glu Glu Phe Asp Ile Val Leu Ser Asp Val His Met Pro Asp Met Asp
        50                  55                  60

Gly Phe Lys Leu Leu Glu Ile Ile Gln Phe Glu Leu Ala Leu Pro Val
65                  70                  75                  80

Leu Met Met Ser Ala Asn Ser Asp Ser Ser Val Val Leu Arg Gly Ile
                85                  90                  95

Ile His Gly Ala Val Asp Tyr Leu Leu Lys Pro Val Arg Ile Glu Glu
            100                 105                 110

Leu Arg Asn Ile Trp Gln His Val Val Arg Arg Asp Tyr Ser Ser Ala
        115                 120                 125

Lys Ser Ser Gly Ser Glu Asp Val Glu Ala Ser Pro Ser Lys Arg
        130                 135                 140

Ala Lys Thr Ser Gly Ser Asn Ser Lys Ser Glu Glu Val Asp Arg Thr
145                 150                 155                 160

Ala Ser Glu Met Ser Ser Gly Lys Ala Arg Lys Lys Pro Thr Gly Lys
                165                 170                 175
```

```
Lys Gly Gly Lys Ser Val Lys Glu Ala Glu Lys Lys Asp Val Val Asp
            180                 185                 190

Asn Ser Asn Ser Lys Lys Pro Arg Val Val Trp Ser Ala Glu Leu His
            195                 200                 205

Ala Gln Phe Val Thr Ala Val Asn Gln Leu Gly Ile Asp Lys Ala Val
            210                 215                 220

Pro Lys Arg Ile Leu Asp Leu Met Gly Val Gln Gly Leu Thr Arg Glu
225                 230                 235                 240

Asn Val Ala Ser His Leu Gln Lys Tyr Arg Leu Tyr Leu Lys Arg Leu
                245                 250                 255

Gln Gly Asn Asp Ala Arg Gly Gly Asn Ala Ser Ser Thr
            260                 265                 270
```

<210> SEQ ID NO 8
<211> LENGTH: 941
<212> TYPE: PRT
<213> ORGANISM: Chlamydomonas reinhardtii
<220> FEATURE:
<221> NAME/KEY: misc_feature
<223> OTHER INFORMATION: SGI1 polypeptide

<400> SEQUENCE: 8

```
Met Asp Ser Gln Gly Val Lys Leu Glu Glu His Pro Gly His Thr Gly
1               5                   10                  15

Gly His Trp Gln Gly Phe Pro Ala Gly Leu Arg Leu Leu Val Val Asp
            20                  25                  30

Asp Asp Pro Leu Cys Leu Lys Val Val Glu Gln Met Leu Arg Lys Cys
            35                  40                  45

Ser Tyr Glu Val Thr Val Cys Ser Asn Ala Thr Thr Ala Leu Asn Ile
        50                  55                  60

Leu Arg Asp Lys Asn Thr Glu Tyr Asp Leu Val Leu Ser Asp Val Tyr
65                  70                  75                  80

Met Pro Asp Met Asp Gly Phe Arg Leu Leu Glu Leu Val Gly Leu Glu
                85                  90                  95

Met Asp Leu Pro Val Ile Met Met Ser Ser Asn Gly Asp Thr Ser Asn
            100                 105                 110

Val Leu Arg Gly Val Thr His Gly Ala Cys Asp Tyr Leu Ile Lys Pro
            115                 120                 125

Val Arg Leu Glu Glu Leu Arg Asn Leu Trp Gln His Val Val Arg Arg
130                 135                 140

Arg Arg Gln His Ala Gln Glu Ile Asp Ser Asp Glu Gln Ser Gln Glu
145                 150                 155                 160

Arg Asp Glu Asp Gln Thr Arg Asn Lys Arg Lys Ala Asp Ala Ala Gly
                165                 170                 175

Val Thr Gly Asp Gln Cys Arg Leu Asn Gly Ser Gly Ser Gly Gly Ala
            180                 185                 190

Ala Gly Pro Gly Ser Gly Gly Ala Gly Gly Met Thr Asp Glu Met
            195                 200                 205

Leu Met Met Ser Gly Gly Glu Asn Gly Ser Asn Lys Lys Ala Arg Val
210                 215                 220

Val Trp Ser Val Glu Met His Gln Gln Phe Val Asn Ala Val Asn Gln
225                 230                 235                 240

Leu Gly Ile Asp Lys Ala Val Pro Lys Lys Ile Leu Glu Ile Met Gly
                245                 250                 255

Val Asp Gly Ser Ala Gly Arg Leu Ala Asp Thr Ser Gly Arg Asp Val
```

-continued

```
                260                 265                 270
Cys Gly Thr Val Tyr Arg Leu Tyr Leu Lys Arg Val Ser Gly Val Thr
            275                 280                 285

Pro Ser Gly His His His Asn Ala Ala His Lys Ser Asn Lys Pro Ser
        290                 295                 300

Pro His Thr Thr Pro Pro Pro Ala Leu Pro Gly Gln Ala Gly Thr
305                 310                 315                 320

His Pro Ala Asn Gln Ala Thr Ala Ile Pro Pro Pro Gln Pro Gly
                325                 330                 335

Ser Gly Thr Ala Ala Gly Ala Ala Ala Ala Gly Thr Gly Gly
            340                 345                 350

Gly Ala Ala Ala Asn Gly His Ala Ala Thr Thr Gly Ala Gly Thr
        355                 360                 365

Pro Gly Ala Ala Pro Gly Ala Gly Gly Val Gly Thr Gly Ala
    370                 375                 380

Gly Gly Leu Gly Ser Gly Pro Asp Gly Ala Ala Ala Ala Gly Pro
385                 390                 395                 400

Gly Pro Gly Ala Ala Val Pro Gly Gly Leu Gly Gly Leu Pro Leu Pro
                405                 410                 415

Pro Gly Ala Gly Pro Gly Pro Gly Gly Phe Gly Gly Pro Ser
            420                 425                 430

Pro Pro Pro Pro Pro His Pro Ala Ala Leu Leu Ala Asn Pro Met Ala
        435                 440                 445

Ala Ala Val Ala Gly Leu Asn Gln Ser Leu Leu Asn Ala Met Gly Ser
450                 455                 460

Leu Gly Val Gly Val Gly Gly Met Ser Pro Leu Gly Pro Val Gly Pro
465                 470                 475                 480

Leu Gly Pro Leu Gly Gly Leu Pro Gly Leu Pro Gly Met Gln Pro Pro
                485                 490                 495

Pro Leu Gly Met Gly Gly Leu Gln Pro Gly Met Gly Pro Leu Gly Pro
            500                 505                 510

Leu Gly Leu Pro Gly Met Gly Gly Leu Pro Gly Leu Pro Gly Met Asn
        515                 520                 525

Pro Met Ala Asn Leu Met Gln Gly Met Ala Ala Gly Met Ala Ala Ala
    530                 535                 540

Asn Gln Met Asn Gly Met Gly Gly His Met Gly Gly His Met Gly Gly
545                 550                 555                 560

Met Asn Gly Pro Met Gly Ala Leu Ala Gly Met Asn Gly Leu Asn Gly
                565                 570                 575

Ala Met Met Gly Gly Leu Pro Gly Met Gly Gly Pro Gln Asn Met Phe
            580                 585                 590

Gln Ala Ala Ala Ala Ala Ala Gln Gln Gln Gln Gln Gln Glu
        595                 600                 605

Gln Gln His Ala Met Met Gln Gln Ala Ala Ala Gly Leu Leu Ala Ser
    610                 615                 620

Gln Gln Gln Gln Gln Gln Gln Gln Gln Gln Gln Gln Gln Gln Ala
625                 630                 635                 640

Leu Gln Gln Gln Gln Gln Gln Gly Met Ala Val Ser Pro Pro Gly Pro
                645                 650                 655

His Asn Ala Thr Pro Asn Gly Gln Leu His Thr His Pro Gln Ala His
            660                 665                 670

His Pro His Gln His Gly Leu His Ala His Ala His Pro His Gln His
        675                 680                 685
```

Leu Asn Thr Ala Pro Ala Gly Ala Leu Gly Leu Ser Pro Pro Gln Pro
690                 695                 700

Pro Ala Gly Leu Leu Ser Ala Ser Gly Leu Ser Ser Gly Pro Asp Gly
705                 710                 715                 720

Ser Gly Leu Gly Ser Gly Val Gly Gly Leu Leu Asp Gly Leu Gln Gln
                725                 730                 735

His Pro His His Pro Gln Leu Gln Leu Ala Gly Ser Leu Gly Thr Gly
            740                 745                 750

Gly Thr Gly Arg Ser Ser Gly Ala Ala Gly Arg Gly Ser Leu Asp Leu
        755                 760                 765

Pro Ala Asp Leu Met Gly Met Ala Leu Leu Asp Phe Pro Pro Val Pro
770                 775                 780

Val Pro Gly Gly Ala Asp Val Gly Met Ala Gly Ala Gly Gly Gly Ala
785                 790                 795                 800

Ala Gly Ala His His His Gly His Gln Gly His Gln Gly Ile Gly Gly
                805                 810                 815

Gly Ala Gly Val Gly Ile Ala Gly Gly Val Gly Cys Gly Val Pro Ala
                820                 825                 830

Ala Ala His Gly Leu Glu Pro Ala Ile Leu Met Asp Asp Pro Ala Asp
            835                 840                 845

Leu Gly Ala Val Phe Ser Asp Val Met Tyr Gly Thr Pro Gly Gly Gly
850                 855                 860

Gly Val Pro Gly Gly Val Pro Gly Gly Val Gly Leu Gly Leu Gly
865                 870                 875                 880

Ala Gly Gln Val Pro Ser Gly Pro Ala Gly Ala Gly Gly Leu His Ser
                885                 890                 895

His His His Gln His His His Gln His His Leu Gly His Val Val
            900                 905                 910

Pro Val Gly Gly Val Asp Pro Leu Ala Gly Asp Ala Ala Lys Met Ala
        915                 920                 925

Met Asn Asp Asp Asp Phe Phe Asn Phe Leu Leu Lys Asn
930                 935                 940

<210> SEQ ID NO 9
<211> LENGTH: 523
<212> TYPE: PRT
<213> ORGANISM: Chromochloris zofingiensis
<220> FEATURE:
<221> NAME/KEY: misc_feature
<223> OTHER INFORMATION: SGI1 polypeptide

<400> SEQUENCE: 9

Met Asp Gly Phe Lys Leu Leu Glu Thr Val Gly Leu Glu Leu Asp Leu
1               5                   10                  15

Pro Val Ile Met Met Ser Ser Asn Gly Glu His Thr Thr Val Met Arg
            20                  25                  30

Gly Val Thr His Gly Ala Cys Asp Phe Leu Ile Lys Pro Val Arg Ile
        35                  40                  45

Glu Glu Leu Arg Asn Ile Trp Gln His Val Ile Arg Arg Thr Arg His
50                  55                  60

Pro Val Phe Arg Asp Leu Glu Pro Asp Asp His Glu Gly Gly Asp Tyr
65                  70                  75                  80

Glu Ala Ser Lys Lys Arg Lys Asp Leu Tyr Arg Gly Glu Asn Ser Ser
                85                  90                  95

Gly Ser Gly Gly Ala Gly Gly Leu Glu Arg Asp Asp Asp Gly Ser Ala

```
              100                 105                 110
Ser Lys Lys Pro Arg Val Val Trp Ser Val Glu Met His Gln Gln Phe
            115                 120                 125
Val Gln Ala Val Asn Gln Leu Gly Ile Asp Lys Ala Val Pro Lys Lys
            130                 135                 140
Ile Leu Glu Leu Met Asn Val Asp Gly Leu Thr Arg Glu Asn Val Ala
145                 150                 155                 160
Ser His Leu Gln Lys Tyr Arg Leu Tyr Leu Lys Arg Val Gln Gly Val
                165                 170                 175
Gln Ala Pro Phe Gly Leu Pro Asn Ile Gln Leu Pro Arg Gln Thr Ser
            180                 185                 190
Ser Lys Gly Ala Gly Ser Ser Gln Gln Gln His His Gln Gln Gln
            195                 200                 205
Gln His Gln Gln Gln His Gln His Gln His Gln Thr Ala Leu Gly Thr
            210                 215                 220
Gly Gln Gln Gln Ser His Gln Leu Gln Pro Cys Pro Val Ser Thr Ala
225                 230                 235                 240
Thr Pro Val Met Pro Ser Pro Asp Ala Met Val Ala Ala Ser Met Met
                245                 250                 255
Ser Ser Gln Ala Met Ala Ala Met Ala Pro Gly Val Met Asn Pro Met
            260                 265                 270
Thr Ala Met Asn Ser Met Met Ala Gly Leu Asn Pro Asn Met Met Gly
            275                 280                 285
Met Ala Ala Gly Leu Gly Leu Ala Gly Leu Gly Ile Gly Gly Met Ala
            290                 295                 300
Gly His Pro Val Pro Asn Pro Met Leu Ala Gly Met Gly Pro Met Gly
305                 310                 315                 320
Leu Gly Leu Pro Pro Pro Gly Met Pro Pro Pro Pro Gly Met
                325                 330                 335
Pro Pro Gly Met Pro Pro Gly Met Pro Pro Gly Met Pro Ala Met Met
            340                 345                 350
Gln Gly Leu Ser Met Ala Gly Met Ser His Leu Ala Ala Ala Gly Met
            355                 360                 365
Arg Pro Pro Gly Ala Leu Gly Gly His Leu Gly Gly Pro Gly Leu
    370                 375                 380
Ser Pro Phe Gly Pro Pro Pro Gly Ala Asp Pro Ala Asn Met
385                 390                 395                 400
Met Ala Asn Met Ser Ser Met Met Ala Asn Met Gln Ala Ala Leu Ala
                405                 410                 415
Phe Gln Ala Asp Ala Ala Ala Ala Gln His Gln Ala Ala Ser Thr
            420                 425                 430
Gly Ser Val Ala Pro Gly Arg Gln Gln Val His Gln His Gln Gln
            435                 440                 445
Ala Val Gly Met Ala Val Asp Asp Ala Ala Phe Pro Ser Pro Gly
            450                 455                 460
Cys Arg Pro Asn Gly Ser Ala Asp Ala Gly Ala Gln Ser Ala Ala Glu
465                 470                 475                 480
Pro Asn Asp Phe Ser Arg Val Phe Asp Pro Phe Ala Gln Pro Ala
                485                 490                 495
Ala Ser Pro Ser Gly Ala Ala Ala Gly Ser Asn Glu Ala Pro Gly
            500                 505                 510
Met Asp Asp Phe Leu Asp Phe Phe Leu Lys Ser
            515                 520
```

```
<210> SEQ ID NO 10
<211> LENGTH: 832
<212> TYPE: PRT
<213> ORGANISM: Volvox carteri
<220> FEATURE:
<221> NAME/KEY: misc_feature
<223> OTHER INFORMATION: SGI1 polypeptide

<400> SEQUENCE: 10

Met Asp Gly Arg Ala Glu Gly Thr Val Ala Ile Lys Gln Glu Asp His
1               5                   10                  15

Ala Ser Gly His Trp His Asn Phe Pro Ala Gly Leu Arg Leu Leu Val
            20                  25                  30

Val Asp Asp Pro Leu Cys Leu Lys Val Val Glu Gln Met Leu Arg
        35                  40                  45

Lys Cys Ser Tyr Asp Val Thr Thr Cys Thr Asn Ala Thr Met Ala Leu
    50                  55                  60

Asn Leu Leu Arg Asp Lys Ser Thr Glu Tyr Asp Leu Val Leu Ser Asp
65                  70                  75                  80

Val Tyr Met Pro Asp Met Asp Gly Phe Lys Leu Leu Glu Val Val Gly
                85                  90                  95

Leu Glu Met Asp Leu Pro Val Ile Met Met Ser Ser Asn Gly Asp Thr
            100                 105                 110

Ser Asn Val Leu Arg Gly Val Thr His Gly Ala Cys Asp Tyr Leu Ile
        115                 120                 125

Lys Pro Val Arg Leu Glu Glu Leu Arg Asn Leu Trp Gln His Val Val
    130                 135                 140

Arg Arg Arg Arg Gln Leu Asn Leu Asp Met Asp Ser Asp Glu His Ser
145                 150                 155                 160

Gln Glu Arg Asp Asp Asp Gln Gly Arg Lys Arg Lys Ala Asp Thr Ala
                165                 170                 175

Gly Cys Ile Gly Asp Gln Leu Arg Met Met Gly Ala Gly Cys Ser Gly
            180                 185                 190

Gly Ala Asn Gly Leu Gly Ser Thr Gly Asn Leu Gly Ala Val Ala Thr
        195                 200                 205

Gly Ser Ala Gly Leu Gly Leu Gly Leu Gly Thr Ala Ala Asp Glu Leu
    210                 215                 220

Gly Leu Gly Leu Asp Asn Gly Ser Ser Lys Lys Ala Arg Val Val Trp
225                 230                 235                 240

Ser Val Glu Met His Gln Gln Phe Val Asn Ala Val Asn Gln Leu Gly
                245                 250                 255

Ile Asp Lys Ala Val Pro Lys Lys Ile Leu Glu Ile Met Asn Val Asp
            260                 265                 270

Gly Leu Thr Arg Glu Asn Val Ala Ser His Leu Gln Lys Tyr Arg Leu
        275                 280                 285

Tyr Leu Lys Arg Val Ser Gly Ala Gln Gln Pro Gly Gln Asn Arg Val
    290                 295                 300

Ser Arg Pro Ser Pro Gln Pro Gln Ser Pro Gln Val Pro Ser Gln
305                 310                 315                 320

Gln Gln Gln Ser Leu Pro Gly Gly Gly Ala Ala Ala Gly Ala
                325                 330                 335

Gly Gln Leu Gln Gly Gly Gly Ala Ala Ala Ala Ser Leu
            340                 345                 350

Ala Ser Ile Leu Ala Gly Gly Gly Pro Ala Gly Gly Gly Ala Gly Ala
```

```
            355                 360                 365
Gly Pro Pro Gly Gly Gly Gln Leu Gly Ala Asp Gly Gly Gly Pro
        370                 375                 380
Gly Pro Gly Leu Ser Ser Ala Val Ala Asn Ala Met Ser Ala Ala
385                 390                 395                 400
Ala Ala Gly Gly Phe Pro Thr Pro Pro Pro Pro Pro His Pro
                405                 410                 415
Ala Ala Leu Leu Ala Ala Asn Pro Met Met Ala Ala Ala Gly Leu
            420                 425                 430
Asn Pro Leu Leu Gly Ala Met Gly Gly Leu Gly Val Gly Pro Leu Gly
            435                 440                 445
Pro Leu Asn Pro Leu Asn Gly Met Pro Met Pro Gly Met Gln Pro Pro
            450                 455                 460
Leu Gly Leu Leu Pro Gly Leu Pro Gly Pro Gly Gly Gln Leu Gly Leu
465                 470                 475                 480
Gly Pro Leu Gly Pro Ile Gly Leu Pro Gly Pro Gly Pro Leu Pro Ser
                485                 490                 495
Leu Pro Ala Gly Leu Pro Leu Asn Pro Met Ala Asn Gly Leu Gln Gln
                500                 505                 510
Met Ala Ala Ala Asn Leu Met Gln Gly Met Ala Gly Met Gly Gln Leu
            515                 520                 525
Pro Ala Leu Ser Met Asn Gly Met Asn Gly Ile Met Gly Pro Leu Pro
            530                 535                 540
Gly Val Gly Leu Pro Gly Pro Gln Gln His Leu Phe Pro Gln Gln Gln
545                 550                 555                 560
Gln Pro His Leu Gln Gln Gln Gln Gln Gln Gln Lys Asp Leu
                565                 570                 575
Gln Met Ala Gln Lys Gln His Gln Ala Ala Ala Ala Ala Ala Val
            580                 585                 590
Ala Ala Ala Val Ala Ala Ala Gln His Gln Gln Gln Pro Gln Ala
            595                 600                 605
Gln Gln Gln Pro Gln Pro Gln Gln Gln Gln Gln Pro Gly Lys Leu
            610                 615                 620
Pro Gln Ala Thr Val Gly Thr Pro Ala Leu Ala Ser Pro Ala Gly Ala
625                 630                 635                 640
Leu Pro Arg Gln Pro Ser Gly Gln His Pro His Thr Leu Ser Ser Ser
                645                 650                 655
Ser Leu His Thr Gln Gln Pro His Gln Gln Gln Leu Leu His Ser Gln
                660                 665                 670
Pro Ser Ser Thr His Leu Ala Thr Asn Asn Thr Leu Ala Met Ala Pro
            675                 680                 685
Ala Leu Asn Gly Thr Leu Asp Val Gly Gly Lys Gly His Leu His Ala
            690                 695                 700
Ala Gly Gly Gln Gly Ala Gly Ala Gly Ala Gly Ala Val Leu Asp Ile
705                 710                 715                 720
Pro Pro Asp Leu Ile Gly Gly Leu Ile Glu Asp Gly Phe Gly Ala Pro
                725                 730                 735
Pro Gly Pro Thr Ile Gln Leu Ala His Gly Thr Ala Ala Val Leu Asp
                740                 745                 750
Pro Thr Met Leu Leu Asp Glu Gly Asp Asn Ser Asp Phe Ala Ala Val
            755                 760                 765
Phe Gln Glu Met Ser Ser Tyr Gly Gly Gly Gly Val Ile Gly Gly Gly
            770                 775                 780
```

```
Gly Ser Gly Ala Gly Ala Met Gly Val Leu Gly His Gly Leu Leu Ala
785                 790                 795                 800

Ala Gly Gly Pro Val Met Val Asp Val Ala Gly Leu Ala Gly Val
            805                 810                 815

Thr Glu Thr Ala Thr Arg Val Asp Asp Asp Phe Leu Asn Phe Leu Leu
            820                 825                 830
```

<210> SEQ ID NO 11
<211> LENGTH: 446
<212> TYPE: PRT
<213> ORGANISM: Tetraselmis sp.
<220> FEATURE:
<221> NAME/KEY: misc_feature
<223> OTHER INFORMATION: SGI1 polypeptide 5172

<400> SEQUENCE: 11

```
Met Ser Cys Thr Val Ala Ser Phe Pro Pro Ala Ala Gly Gly Gln Gly
1               5                   10                  15

Ser Pro Ala Thr Pro Val Pro Tyr Gln Asp Leu Leu Val Lys Arg Gln
            20                  25                  30

Asp Gln Trp Ser Asn Phe Pro Ala Gly Leu Arg Val Leu Val Ala Asp
        35                  40                  45

Asn Asp Pro Ala Ser Leu Gln Gln Val Glu Lys Met Leu Lys Lys Cys
50                  55                  60

Ser Tyr Gln Val Thr Leu Cys Ser Ser Gly Lys Asn Ser Leu Glu Ile
65                  70                  75                  80

Leu Arg Lys Arg Arg Glu Glu Phe Asp Leu Val Leu Ala Asp Ala Asn
                85                  90                  95

Leu Pro Asp Ile Asp Gly Phe Lys Leu Leu His Val Cys His Thr Glu
            100                 105                 110

Leu Ser Leu Pro Val Val Leu Met Ser Gly Thr Ser Asp Thr Gln Leu
        115                 120                 125

Val Met Arg Gly Val Met Asp Gly Ala Arg Asp Phe Leu Ile Lys Pro
    130                 135                 140

Leu Arg Val Glu Glu Leu Lys Val Leu Trp Gln His Leu Val Arg Phe
145                 150                 155                 160

Thr Ser Glu Ile Thr Lys Thr Asp Ala Gln Leu Asn Val Val Lys Val
                165                 170                 175

Glu Leu Asp Gly Gly Arg Pro Ala Gly Glu Val Ser Thr Ser Gln Asn
            180                 185                 190

Gly Ser Gln Cys Thr Glu Arg Glu Gly Glu Gly Asn Ser Ser Lys Lys
        195                 200                 205

Gln Arg Met Asn Trp Ser Asp Glu Met His Gln Gln Phe Val Asn Ala
    210                 215                 220

Val Asn Gln Leu Gly Ile Asp Lys Ala Val Pro Lys Arg Ile Leu Asp
225                 230                 235                 240

Leu Met Ser Val Glu Gly Leu Thr Arg Glu Asn Val Ala Ser His Leu
                245                 250                 255

Gln Lys Tyr Arg Ile Tyr Leu Lys Arg Met Ala Asn His Gln Glu Asn
            260                 265                 270

Gly Lys Gln Ala Val Met Ser Thr Asp Thr Ile Ala Arg Ala Glu Ala
        275                 280                 285

Ala Tyr Gln Gly Gly Met Pro Gln Gly Gln Gln Met Met Gln Gln Glu
    290                 295                 300

His Ser Gly Gln Ala Val Gln Tyr Ser Gln Pro His Ala Pro Gly Gly
```

```
305                 310                 315                 320
Leu His Gln Gln Ala Met Pro Ala Gln Met His Met Gly Met Met Pro
                325                 330                 335

Ala Gly Pro Gln Pro Gly Ser Met Gln Met Ala Pro His His Val Met
                340                 345                 350

Gln Met Pro Asn Gly Gln Val Met Val Met Gln Gln Met Gly Pro Arg
                355                 360                 365

Pro Gly Met Pro Pro Gly Met Pro Gln Gln Met Met Ala Ser Ser Gln
                370                 375                 380

Gln Met Gly Met Leu Gln Pro Gly Met Pro Ala Gly Gln Met Leu His
385                 390                 395                 400

Phe Gln His Pro Gln Gln Val His Gln His Pro Pro Ser Ser Gly Pro
                405                 410                 415

Met His Ala Val Gln His Met Glu Tyr Ala Tyr Ser Gln Pro Met Gln
                420                 425                 430

Met Ala Gly Trp Pro Val Gln Gly Gln Pro Gly Asn Gln Ala
                435                 440                 445

<210> SEQ ID NO 12
<211> LENGTH: 490
<212> TYPE: PRT
<213> ORGANISM: Tetraselmis sp.
<220> FEATURE:
<221> NAME/KEY: misc_feature
<223> OTHER INFORMATION: SGI1 polypeptide 5185

<400> SEQUENCE: 12

Met Thr Pro Thr Pro Pro Met Ser Cys Thr Val Ala Ser Phe Pro Pro
1               5                   10                  15

Ala Ala Gly Gly Gln Gly Ser Pro Ala Thr Pro Val Pro Tyr Gln Asp
                20                  25                  30

Leu Leu Val Lys Arg Gln Asp Gln Trp Ser Asn Phe Pro Ala Gly Leu
                35                  40                  45

Arg Val Leu Val Ala Asp Asn Asp Pro Ala Ser Leu Gln Gln Val Glu
                50                  55                  60

Lys Met Leu Lys Lys Cys Ser Tyr Gln Val Thr Leu Cys Ser Ser Gly
65                  70                  75                  80

Lys Asn Ser Leu Glu Ile Leu Arg Lys Arg Arg Glu Glu Phe Asp Leu
                85                  90                  95

Val Leu Ala Asp Ala Asn Leu Pro Asp Ile Asp Gly Phe Lys Leu Leu
                100                 105                 110

His Val Cys His Thr Glu Leu Ser Leu Pro Val Val Leu Met Ser Gly
                115                 120                 125

Thr Ser Asp Thr Gln Leu Val Met Arg Gly Val Met Asp Gly Ala Arg
                130                 135                 140

Asp Phe Leu Ile Lys Pro Leu Arg Val Glu Glu Leu Lys Val Leu Trp
145                 150                 155                 160

Gln His Leu Val Arg Phe Thr Ser Glu Ile Thr Lys Thr Asp Ala Gln
                165                 170                 175

Leu Asn Val Val Lys Val Glu Leu Asp Gly Gly Arg Pro Ala Gly Glu
                180                 185                 190

Val Ser Thr Ser Gln Asn Gly Ser Gln Cys Thr Glu Arg Glu Gly Glu
                195                 200                 205

Gly Asn Ser Ser Lys Lys Gln Arg Met Asn Trp Ser Asp Glu Met His
                210                 215                 220
```

```
Gln Gln Phe Val Asn Ala Val Asn Gln Leu Gly Ile Asp Lys Ala Val
225                 230                 235                 240

Pro Lys Arg Ile Leu Asp Leu Met Ser Val Glu Gly Leu Thr Arg Glu
            245                 250                 255

Asn Val Ala Ser His Leu Gln Lys Tyr Arg Ile Tyr Leu Lys Arg Met
        260                 265                 270

Ala Asn His Gln Glu Asn Gly Lys Gln Ala Val Met Ser Thr Asp Thr
    275                 280                 285

Ile Ala Arg Ala Glu Ala Tyr Gln Gly Gly Met Pro Gln Gly Gln
290                 295                 300

Gln Met Met Gln Gln Glu His Ser Gly Gln Ala Val Gln Tyr Ser Gln
305                 310                 315                 320

Pro His Ala Pro Gly Gly Leu His Gln Gln Ala Met Pro Ala Gln Met
            325                 330                 335

His Met Gly Met Met Pro Ala Gly Pro Gln Pro Gly Ser Met Gln Met
        340                 345                 350

Ala Pro His His Val Met Gln Met Pro Asn Gly Gln Val Met Val Met
    355                 360                 365

Gln Gln Met Gly Pro Arg Pro Gly Met Pro Pro Gly Met Pro Gln Gln
370                 375                 380

Met Met Ala Ser Ser Gln Gln Met Gly Met Leu Gln Pro Gly Met Pro
385                 390                 395                 400

Ala Gly Gln Met Leu His Phe Gln His Pro Gln Gln Val His Gln His
            405                 410                 415

Pro Pro Ser Ser Gly Pro Met His Ala Gly Gly Glu Met Ile Asp Pro
        420                 425                 430

Gly Ser Met Gln Arg Leu His Gln Gln Pro His Tyr Ile Gly Pro Asn
    435                 440                 445

Gly Gln His Met Pro Ala Pro Ala Met Gly Met Pro Ser Gly Thr Val
450                 455                 460

Gln His Met Glu Tyr Ala Tyr Ser Gln Pro Met Gln Met Ala Gly Trp
465                 470                 475                 480

Pro Val Gln Gly Gln Pro Gly Asn Gln Ala
            485                 490
```

<210> SEQ ID NO 13
<211> LENGTH: 574
<212> TYPE: PRT
<213> ORGANISM: Tetraselmis sp.
<220> FEATURE:
<221> NAME/KEY: misc_feature
<223> OTHER INFORMATION: SGI1 polypeptide 5230

<400> SEQUENCE: 13

```
Met Thr Met Pro Leu Gly Gly Gly Leu Cys Met Lys Asp Arg Ile His
1               5                   10                  15

Gly Asp Glu Arg Tyr Arg Ser Lys Ala Lys Arg Gln Val Asn Thr Ile
            20                  25                  30

Phe Ala Phe Thr Gln Arg Asn Thr Trp Arg Gly Arg Phe Arg Leu Cys
        35                  40                  45

Ser Tyr Arg Thr Thr Glu Leu Leu Gly Gly Ser Lys Thr Thr Glu Pro
    50                  55                  60

Gly Arg Gly Thr Phe Val Leu Gln Ile Phe Met Cys Val Lys Asn Ala
65                  70                  75                  80

Ser Ile Asp Asp Gly Ser Arg His Ile Ser Thr Ser Arg Gly Leu Glu
                85                  90                  95
```

```
Ser Val Leu Lys Arg Arg Gly Gln Gly Ala Pro Ala Ala Pro Val
            100                 105                 110

Pro Tyr His Asp Leu Leu Val Lys Arg Gln Asp Gln Trp Ser Asn Phe
            115                 120                 125

Pro Ala Gly Leu Arg Val Leu Val Ala Asp Asn Asp Pro Ala Ser Leu
            130                 135                 140

Gln Gln Val Glu Lys Met Leu Lys Lys Cys Ser Tyr Gln Val Thr Leu
145                 150                 155                 160

Cys Ser Ser Gly Lys Asn Ser Leu Glu Ile Leu Arg Lys Arg Arg Glu
                165                 170                 175

Glu Phe Asp Leu Val Leu Ala Asp Ala Asn Leu Pro Asp Ile Asp Gly
            180                 185                 190

Phe Lys Leu Leu His Val Cys His Thr Glu Leu Ser Leu Pro Val Val
            195                 200                 205

Leu Met Ser Gly Thr Ser Asp Thr Gln Leu Val Met Arg Gly Val Met
    210                 215                 220

Asp Gly Ala Arg Asp Phe Leu Ile Lys Pro Leu Arg Val Glu Glu Leu
225                 230                 235                 240

Lys Val Leu Trp Gln His Leu Val Arg Phe Thr Ser Glu Ile Thr Lys
                245                 250                 255

Thr Asp Ala Gln Leu Asn Val Val Lys Val Glu Leu Asp Ser Gly Arg
            260                 265                 270

Pro Ala Gly Glu Val Ser Thr Ser Gln Asn Gly Ser Gln Cys Ala Glu
            275                 280                 285

Arg Glu Gly Glu Gly Asn Ser Ser Lys Lys Gln Arg Met Asn Trp Ser
            290                 295                 300

Asp Glu Met His Gln Gln Phe Val Asn Ala Val Asn Gln Leu Gly Ile
305                 310                 315                 320

Asp Lys Ala Val Pro Lys Arg Ile Leu Asp Leu Met Ser Val Glu Gly
                325                 330                 335

Leu Thr Arg Glu Asn Val Ala Ser His Leu Gln Lys Tyr Arg Ile Tyr
            340                 345                 350

Leu Lys Arg Met Ala Asn His Gln Glu Asn Gly Lys Gln Ala Val Met
            355                 360                 365

Ser Thr Asp Thr Ile Ala Arg Ala Glu Ala Ala Tyr Gln Gly Gly Met
    370                 375                 380

Pro Gln Gly Gln Gln Met Met Gln Gln Glu His Ser Gly Gln Ala Val
385                 390                 395                 400

Gln Tyr Ser Gln Pro His Ala Pro Ser Gly Leu His Gln Ala Met
                405                 410                 415

Pro Ala Gln Met His Met Gly Met Met Pro Ala Gly Pro Gln Pro Gly
            420                 425                 430

Ser Met Gln Met Ala Pro His His Val Met Gln Met Pro Asn Gly Gln
            435                 440                 445

Val Met Val Met Gln Gln Met Gly Pro Arg Pro Gly Met Pro Pro Gly
            450                 455                 460

Met Pro Gln Gln Met Met Ala Ser Ser Gln Gln Met Gly Met Leu Gln
465                 470                 475                 480

Pro Gly Met Pro Ala Gly Gln Met Leu His Phe Gln His Pro Gln Gln
                485                 490                 495

Val His Gln His Pro Pro Ser Ser Gly Pro Met His Ala Gly Gly Glu
            500                 505                 510
```

```
Met Ile Asp Pro Gly Ser Met Gln Arg Leu His Gln Pro His Tyr
        515                 520                 525
Ile Val Pro Asn Ala Gln His Met Pro Ala Pro Ala Met Gly Met Pro
    530                 535                 540
Pro Gly Ala Val Gln His Met Glu Tyr Ala Tyr Ser Gln Pro Met Gln
545                 550                 555                 560
Met Ala Gly Trp Pro Val Gln Gly Gln Pro Gly Ser Gln Ala
                565                 570

<210> SEQ ID NO 14
<211> LENGTH: 674
<212> TYPE: PRT
<213> ORGANISM: Oocystis sp.
<220> FEATURE:
<221> NAME/KEY: misc_feature
<223> OTHER INFORMATION: SGI1 polypeptide 5549

<400> SEQUENCE: 14

Met Leu Ala Phe Thr His Gln Arg Met Thr Thr Ala Pro Ala Leu Ala
1               5                   10                  15
Val Ala Thr Ser His Phe Phe Ala His Val Arg Val Thr Thr Gly Ser
            20                  25                  30
Ser Ala Ile Ala Thr Val Phe Ala Ala Arg Ser Arg Gly Ser Gly Leu
        35                  40                  45
Leu Ala Gly Phe Asn Thr Met Glu Asn Val Lys Val Glu Val Pro Glu
    50                  55                  60
Val Val Pro Glu Asn Val Asn Phe Pro Ala Gly Leu Lys Val Leu Val
65                  70                  75                  80
Val Asp Asp Asp Pro Leu Cys Leu Lys Val Ile Asp Gln Met Leu Arg
                85                  90                  95
Arg Cys Asn Tyr Ala Ala Thr Thr Cys Gln Ser Ser Leu Glu Ala Leu
            100                 105                 110
Glu Leu Leu Arg Ser Ser Lys Glu Asn His Phe Asp Leu Val Leu Ser
        115                 120                 125
Asp Val Tyr Met Pro Asp Met Asp Gly Phe Lys Leu Leu Glu Ile Ile
    130                 135                 140
Gly Leu Glu Met Gly Leu Pro Val Ile Met Met Ser Ser Asn Gly Glu
145                 150                 155                 160
Thr Gly Val Val Phe Arg Gly Val Thr His Gly Ala Val Asp Phe Leu
                165                 170                 175
Ile Lys Pro Val Arg Ile Glu Glu Leu Arg Asn Leu Trp Gln His Val
            180                 185                 190
Val Arg Lys Thr Met Val Val Pro Ser Asn Asp Lys Ala Thr Ser Glu
        195                 200                 205
Glu Asp Gly Glu Glu Ser Lys His Arg Val Asp Arg Lys Arg Lys Glu
    210                 215                 220
Ser Phe His Ser Arg Ala Arg Glu Gln Val Glu Ile Ala Cys Ser Val
225                 230                 235                 240
Val Pro Ala Leu Leu Trp Pro Thr Val Pro Pro Ser Ser Val His Pro
                245                 250                 255
Thr Ser Ser Ser Phe Leu Arg Ser His Val Leu Leu Leu Gln Arg Ser
            260                 265                 270
Ser Gly Gly Lys Asp Val Leu Asp Glu Gly Gly Ser Asn Ala Lys Lys
        275                 280                 285
Pro Arg Val Val Trp Ser Val Glu Met His Gln Gln Phe Val Asn Ala
    290                 295                 300
```

Val Asn Gln Leu Gly Ile Asp Lys Ala Val Pro Lys Arg Ile Leu Asp
305                 310                 315                 320

Leu Met Asn Val Asp Gly Leu Thr Arg Glu Asn Val Ala Ser His Leu
            325                 330                 335

Gln Lys Tyr Arg Leu Tyr Leu Lys Arg Val Ala Gly Ile Asn Thr Ala
        340                 345                 350

Thr Gly Ser Arg Asn Gly Lys Gly Arg Ser Asp Val Ser Gly Leu Ser
    355                 360                 365

Gly Met Pro Asn Gly Ser Leu Pro Met Pro Gly Met Met Pro Pro His
370                 375                 380

Met Ala Ala Gly Met Leu Leu Ala Gly Met Ala Ala Asp Val Gly Pro
385                 390                 395                 400

Arg Pro His Pro Phe Pro Ile Met Pro Met Pro Ala Met Ala Leu Gln
                405                 410                 415

Gly Met His Gly Gly Met Ala Gln Met Met Gln Leu Pro Pro Gly Met
            420                 425                 430

Pro Pro Pro Met Met Met Pro Met Ala Pro Leu Leu Pro Ser Gln Leu
        435                 440                 445

Ala Ala Leu Gly Gln Gln Gln Gln Gln Gln Gln Gln Gln Gln Val Ala
    450                 455                 460

Arg Ser Glu Ser Met Pro Ser Glu Asn Gly Val Ala Gly Pro Ser Gly
465                 470                 475                 480

Ser Phe Thr Ala Met Leu Asn Gly Pro Ala Pro Met Glu Ser Ser Pro
                485                 490                 495

Phe Ala Ala Leu Gln Val Phe Gly Pro Pro Gln Gly Met Glu Gln Leu
            500                 505                 510

Thr Gln Gln Gln Gln Gln Gln Gln Ala Gly Ala Ala Ala Phe Val
        515                 520                 525

Ala Ala Phe Ala Ala Ala Asn Gly Gly Asp Met Gln Gly Gly Gly Gly
    530                 535                 540

Gly Pro Gly Pro Met Leu Gly Gly Ala Gly Gly Ala Gly Pro Leu Leu
545                 550                 555                 560

Gly Gly Val Gly Gly Gly Asp Pro Leu His Gly Gly Gly Ser Ser
                565                 570                 575

Ala Leu Gly Gly Arg Pro Met Met Ser Ala Glu Gln Pro Met Gly Gly
            580                 585                 590

Ser Gly Gly Leu Ala Ser Asn Ser Leu Thr Val Gln Gln Asn Asp Leu
        595                 600                 605

Ala Gln Met Cys Ser Gln Leu Asp Val Asn Gly Leu Gln Ala Val Ala
    610                 615                 620

Ala Ala Ala Ala Ala Gly Ala Met Gly Ala Pro Gly Gly Ala Gly Gly
625                 630                 635                 640

Ala Met Pro Pro Ser Ser Val Gly Gly Val Gly Pro Asp Met Lys Leu
                645                 650                 655

Thr Glu Gln Asp Asp Phe Phe Ser Phe Leu Leu Lys Asp Ser Asn Leu
            660                 665                 670

Ile Asp

<210> SEQ ID NO 15
<211> LENGTH: 488
<212> TYPE: PRT
<213> ORGANISM: Micromonas sp.
<220> FEATURE:
<221> NAME/KEY: misc_feature
<223> OTHER INFORMATION: RCC299, SGI1 polypeptide

<400> SEQUENCE: 15

```
Met Ser Thr Pro Ala Val Ser Lys Gly Phe Pro Ile Gly Leu Arg Val
1               5                   10                  15

Leu Val Val Asp Asp Pro Leu Cys Leu Lys Ile Val Glu Lys Met
            20                  25                  30

Leu Lys Arg Cys Gln Tyr Glu Val Thr Thr Phe Ser Arg Gly Ala Glu
            35                  40                  45

Ala Leu Lys Thr Leu Arg Glu Arg Lys Asp Asp Phe Asp Ile Val Leu
50                  55                  60

Ser Asp Val His Met Pro Asp Met Asp Gly Phe Lys Leu Leu Glu His
65                  70                  75                  80

Ile Ala Leu Glu Leu Asp Ile Pro Val Met Met Met Ser Ala Asn Cys
                85                  90                  95

Ala Thr Asp Val Val Leu Arg Gly Ile Ile His Gly Ala Val Asp Tyr
            100                 105                 110

Leu Leu Lys Pro Val Arg Ile Glu Glu Leu Arg Asn Ile Trp Gln His
            115                 120                 125

Val Val Arg Arg Lys Arg Glu Ser Ser Gln Gly Asn Leu Arg Ser Gly
130                 135                 140

Glu Gly Gly Ser Asn Gly Arg Thr Val Ser Gly Gly Ser Thr Gly Glu
145                 150                 155                 160

Gly Gly Gly Lys Asp Ser Lys Gly Ser Ser Glu Gln His Gly Asp Ala
                165                 170                 175

Lys Asp Lys Thr Gly Ser Ala Gly Ser Gly Gly Ser Ser Lys Arg
            180                 185                 190

Lys Lys Gly Ser Gly Lys Lys Gly Asp Glu Gly Thr Asp Glu Val Lys
            195                 200                 205

Asp Gly Ser Gly Gly Asp Glu Asn Glu Asp Ser Ser Ala Leu Lys Lys
210                 215                 220

Pro Arg Val Val Trp Ser Ala Glu Leu His Gln Gln Phe Val Thr Ala
225                 230                 235                 240

Val Asn Gln Leu Gly Ile Asp Lys Ala Val Pro Lys Arg Ile Leu Asp
                245                 250                 255

Leu Met Gly Val Gln Gly Leu Thr Arg Glu Asn Val Ala Ser His Leu
            260                 265                 270

Gln Lys Tyr Arg Leu Tyr Leu Lys Arg Leu Gln Gly Val Asn Ser Gly
            275                 280                 285

Gly Ala Pro Gly Gly Pro Gly Phe Met Ser Pro Ile Ala Leu Asp
290                 295                 300

Gly Ser Met Val Gln Gly Pro Gly Gly Arg Val Gly Ser Pro Ala
305                 310                 315                 320

Ile Gly Gly Pro Asn Gly Pro Ile Met Val Gly His Gly His Ile Asp
                325                 330                 335

Pro Ala Met Leu Ala Gly Gly Ala Pro Gln Thr Ile Gln Met Gly Met
            340                 345                 350

Val Tyr Gly Gly Pro Gly Met Gly Pro Pro Gln Met Met Ala Pro Asn
            355                 360                 365

Gly Lys Gly Gly Gly Met Pro Gly Gly Tyr Val Met Gln Pro Gly
370                 375                 380

Gln Met Met Ala Pro Asn Gly Gln Met Met Pro Val Gly Gln Met Gly
385                 390                 395                 400
```

```
Pro Gly Gly Met Met Val Gln Gly Pro Gly Gly Met Met Gln Met
            405                 410                 415

His Asp Gly Gly Met Met Asn Gly Asn Gly Ser Tyr Gly Ser Leu Gln
                420                 425                 430

Asn Met Lys Gln Gly Asn Gly Val Val Met Met Pro Asn Gly Gly Met
            435                 440                 445

Gly Gly Val Asp Gly Ala Ile Pro Asn Met Ala Thr Gly Leu Ile Asn
            450                 455                 460

Gly Gln Gly Leu Pro Asp Asp Asp Val Leu Asp Met Phe Leu Lys Asp
465                 470                 475                 480

Gly Leu Pro Glu Gly Glu Gly Phe
                485
```

<210> SEQ ID NO 16
<211> LENGTH: 544
<212> TYPE: PRT
<213> ORGANISM: Micromonas pusilla
<220> FEATURE:
<221> NAME/KEY: misc_feature
<223> OTHER INFORMATION: SGI1 polypeptide

<400> SEQUENCE: 16

```
Met Thr Ala Glu Lys Glu Leu Lys Val Phe Pro Ala Gly Leu Arg
1               5                   10                  15

Val Leu Val Val Asp Asp Pro Leu Cys Leu Arg Ile Val Glu Lys
            20                  25                  30

Met Leu Lys Arg Cys Gln Tyr Glu Val Thr Thr Phe Ser Arg Gly Ala
            35                  40                  45

Glu Ala Leu Glu Thr Leu Arg Ala Arg Arg Asp Asp Phe Asp Ile Val
50                  55                  60

Leu Ser Asp Val His Met Pro Asp Met Asp Gly Phe Lys Leu Leu Glu
65                  70                  75                  80

His Ile Ala Leu Glu Leu Asp Val Pro Val Met Met Met Ser Ala Asn
            85                  90                  95

Cys Ala Thr Asp Val Val Leu Arg Gly Ile Ile His Gly Ala Val Asp
            100                 105                 110

Tyr Leu Leu Lys Pro Val Arg Leu Glu Glu Leu Arg Asn Ile Trp Gln
            115                 120                 125

His Val Val Arg Arg Gln Arg Glu Pro Ser Lys Asp Gly Ala Ala Gly
            130                 135                 140

Lys Gly Gly Gly Ala Ser Gly Ala Pro Glu Val Ser Gly Asp Thr His
145                 150                 155                 160

Ala Asn Thr Asp Asp Lys Gln Asp Gly Asn Ala Thr Asp Ser Lys Gly
                165                 170                 175

Ser Gly Ser Gln Lys Arg Lys Ser Gly Lys Ser Gly Asp Gly Gly
            180                 185                 190

Lys Asp Gly Gly Ser Gly Gly Lys Asp Gly Asp Ala Ser Asn Lys
            195                 200                 205

Gly Asn Asn Asn Lys Arg Lys Lys Gly Lys Ser Asn Asp Ala Thr Glu
            210                 215                 220

Thr Ala Gly Gly Ala Gly Val Glu Asp Asn Asp Asp Thr Ser Gly Leu
225                 230                 235                 240

Lys Lys Pro Arg Val Val Trp Ser Pro Glu Leu His Gln Gln Phe Val
            245                 250                 255

Thr Ala Val Asn Gln Leu Gly Ile Asp Lys Ala Val Pro Lys Arg Ile
            260                 265                 270
```

-continued

```
Leu Asp Leu Met Gly Val Gln Gly Leu Thr Arg Glu Asn Val Ala Ser
    275                 280                 285

His Leu Gln Lys Tyr Arg Leu Tyr Leu Lys Arg Leu Gln Gly Val Asn
    290                 295                 300

Asn Asn Gly Thr Val Pro Ser Gly Ala Ala Gly Phe Met Thr Gly Leu
305                 310                 315                 320

Ala Ile Asp Gly Val Gly Gly Val Met Gly Pro Pro Thr Thr Gly Ser
                325                 330                 335

Pro Ala Met Asn Gly Pro Gly Gly Pro Gly Gly Gly Leu Val Met Gly
                340                 345                 350

Pro Gly His Met Gly Gly Pro His Met Asp Gly Ser Gly Met Met His
            355                 360                 365

Met Gly Pro Gly Gly Pro Met Ala Gly Met Thr Val Val Tyr Gly Gly
    370                 375                 380

Gly Met Pro Gly Gly Met Pro Gly Gly Ala Asp Ser Lys Asn Gly Ala
385                 390                 395                 400

Ser Gly Gln Pro Pro Pro Gly Gly Tyr Val Val Met Gly Gly Pro His
                405                 410                 415

Gly Gly Gly Pro Gly Gly Ala Pro Met Met Met Gln His Gly Gly Met
                420                 425                 430

Val Pro Gly Pro Gly Pro Gly Leu Val Pro Gly Pro Gly Gly Ser Leu
                435                 440                 445

Met Met Pro Ala Gly Met Met Pro Asp Gly Gly Gly Met Val Gly
    450                 455                 460

Val His Val Gly Pro Gly Val Val Met Gly Gln His Gln Leu Gly Gly
465                 470                 475                 480

Lys His Ser Ser Gly Gly Ala Gly Met Ala Gly Gly Ser Ala Ala Gly
                485                 490                 495

Lys Gly Ala Gln Arg Gly Gly Val Gly Gly Ala Phe Asp Val Pro Pro
                500                 505                 510

Thr Asn Gly Ser Leu Asp Ala Asp Glu Ile Gly Asp Asp Val Leu Thr
            515                 520                 525

Met Phe Leu Lys Asp Gly Leu Pro Glu Met Asn Asp Gly Asp Ala Leu
    530                 535                 540
```